US008353899B1

(12) United States Patent
Wells et al.

(10) Patent No.: US 8,353,899 B1
(45) Date of Patent: Jan. 15, 2013

(54) MULTIPLE-MODE DEVICE FOR HIGH-POWER SHORT-PULSE LASER ABLATION AND CW CAUTERIZATION OF BODILY TISSUES

(75) Inventors: Jonathon D. Wells, Seattle, WA (US); Mark P. Bendett, Kirkland, WA (US); Matthias P. Savage-Leuchs, Seattle, WA (US); James M. Owen, Redmond, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 13/526,524

(22) Filed: Jun. 19, 2012

Related U.S. Application Data

(62) Division of application No. 12/050,937, filed on Mar. 18, 2008, now Pat. No. 8,202,268.

(60) Provisional application No. 60/895,480, filed on Mar. 18, 2007.

(51) Int. Cl.
*A61B 18/20* (2006.01)
(52) U.S. Cl. .................. 606/10; 606/9; 359/238
(58) Field of Classification Search .......... 359/238; 606/9–15
See application file for complete search history.

(56) References Cited

U.S. PATENT DOCUMENTS

| | | | |
|---|---|---|---|
| 4,733,660 A | 3/1988 | Itzkan | |
| 5,021,452 A | 6/1991 | Labbe et al. | |
| 5,071,417 A | 12/1991 | Sinofsky et al. | |
| 5,112,328 A | 5/1992 | Taboada et al. | |
| 5,140,984 A | 8/1992 | Dew et al. | |
| 5,151,098 A | 9/1992 | Loertscher | |
| 5,363,387 A | 11/1994 | Sinofsky | |
| 5,459,745 A | 10/1995 | Esterowitz et al. | |
| 5,546,214 A | 8/1996 | Black | |
| 5,616,140 A | 4/1997 | Prescott | |
| 5,656,186 A | 8/1997 | Mourou et al. | |
| 5,662,643 A | 9/1997 | Kung et al. | |
| 5,769,840 A | 6/1998 | Schirmer | |
| 5,775,572 A | 7/1998 | Oliff | |

(Continued)

FOREIGN PATENT DOCUMENTS

WO    WO 2007080239    7/2007

OTHER PUBLICATIONS

Topping, et al., "Successful reduction in skin damage resulting from exposure to the normal-mode ruby laser in an animal model", "British Journal of Plastic Surgery", 2001, pp. 144-150, vol. 54.

(Continued)

*Primary Examiner* — Ahmed M Farah
*Assistant Examiner* — Jeffrey Lipitz
(74) *Attorney, Agent, or Firm* — Charles A. Lemaire; Jonathan M. Rixen; Lemaire Patent Law Firm, P.L.L.C.

(57) ABSTRACT

An apparatus and process using a high-power, short-pulsed thulium laser to output infrared laser pulses delivered through an optical fiber, for cutting and ablating biological tissue. In some embodiments, the pulse length is shortened sufficiently to keep inside the stress-confined ablation region of operation. In some embodiments, the pulse is shortened to near the stress-confined ablation region of operation, while being slightly in the thermal-constrained region of operation. In some embodiments, the laser is coupled to a small low —OH optical fiber (~100 μm diameter). In some embodiments, the device has a pulse duration of about 100 ns for efficient ablation; however in some embodiments, this parameter is adjustable.

20 Claims, 12 Drawing Sheets

U.S. PATENT DOCUMENTS

| | | | |
|---|---|---|---|
| 5,897,549 | A | 4/1999 | Tankovich |
| 5,993,378 | A | 11/1999 | Lemelson |
| 6,074,382 | A | 6/2000 | Asah et al. |
| 6,083,217 | A | 7/2000 | Tankovich |
| 6,096,031 | A | 8/2000 | Mitchell et al. |
| 6,165,205 | A | 12/2000 | Neuberger |
| 6,228,076 | B1 | 5/2001 | Winston et al. |
| 6,267,779 | B1 | 7/2001 | Gerdes |
| 6,310,900 | B1 | 10/2001 | Stephens et al. |
| 6,395,000 | B1 | 5/2002 | Mitchell et al. |
| 6,529,543 | B1 | 3/2003 | Anderson et al. |
| 6,572,637 | B1 | 6/2003 | Yamazaki et al. |
| 6,723,090 | B2 | 4/2004 | Altshuler et al. |
| 6,984,228 | B2 | 1/2006 | Anderson et al. |
| 6,997,923 | B2 | 2/2006 | Anderson et al. |
| 7,051,738 | B2 | 5/2006 | Oron et al. |
| 7,137,395 | B2 | 11/2006 | Fried et al. |
| 7,177,695 | B2 | 2/2007 | Moran |
| 7,260,299 | B1 | 8/2007 | Di Teodoro et al. |
| 7,292,232 | B2 | 11/2007 | Ranta et al. |
| 7,351,252 | B2 | 4/2008 | Altshuler et al. |
| 7,391,561 | B2 | 6/2008 | Di Teodoro et al. |
| 7,620,077 | B2 | 11/2009 | Henderson |
| 7,988,688 | B2 | 8/2011 | Webb et al. |
| 7,988,689 | B2 | 8/2011 | Dahla et al. |
| 2002/0045811 | A1 | 4/2002 | Kitterell et al. |
| 2004/0199151 | A1 | 10/2004 | Neuberger |
| 2004/0236319 | A1 | 11/2004 | Davenport et al. |
| 2005/0049582 | A1 | 3/2005 | DeBenedictis et al. |
| 2006/0016790 | A1 | 1/2006 | Yeik |
| 2006/0020309 | A1 | 1/2006 | Altshuler et al. |
| 2006/0122668 | A1 | 6/2006 | Anderson et al. |
| 2007/0073308 | A1 | 3/2007 | Anderson et al. |
| 2007/0219605 | A1 | 9/2007 | Yaroslavsky et al. |
| 2007/0264625 | A1 | 11/2007 | DeBenedictis et al. |
| 2007/0264626 | A1 | 11/2007 | DeBenedictis et al. |
| 2007/0265606 | A1 | 11/2007 | DeBenedictis et al. |
| 2008/0077200 | A1 | 3/2008 | Bendett et al. |
| 2008/0086118 | A1 | 4/2008 | Lai et al. |

OTHER PUBLICATIONS

Vogel, Alfred, et al., "Mechanisms of pulsed laser ablation of biological tissues.", "Chemical Reviews", 2003, pp. 577-644, vol. 103, No. 2.

Vogel, Alfred et al., "Minimization of thermomechanical side effects and increase of ablation efficiency in IR ablation by use of multiply Q-sw", "Proceedings of SPIE", 2002, pp. 105-111, vol. 4617.

Wilmink, et al., "Wavelength-dependent dynamics of heat shock protein 70 expression in free electron laser wounds.", "Thermal Treatment of Tissue: Energy Delivery and Assessment IV (Ryan TP ed) SPIE: San Jose, CA, USA", 2007, pp. 644003-644012.

Wilmink, et al., "Assessing laser-tissue damage with bioluminescent imaging", "J. Biomed. Opt", 2006, pp. 041114, vol. 11.

Beckham, J.T., et al., "Assessment of cellular response to thermal laser injury through bioluminescence imaging of heat shock protein 70.", "Photochem. Photobiol", 2004, pp. 76-85, vol. 79.

Bowman, P.D., et al. , "Survival of human epidermal keratinocytes after short-duration high temperature: synthesis of HSP70 and IL-8", Jun. 1997, pp. C1988-1994, vol. 272, Publisher: Am. J. Physiol.

Braddock, Martin, et al. , "Current therapies for wound healing: electrical stimulation, biological therapeutics, and the potential for gene therapy", "Int. J. Dermatol.", 1999, pp. 808-817, vol. 38.

Cao, Yu, et al., "TGF-beta1 mediates 70-kDa heat shock protein induction due to ultraviolet irradiation in human skin fibroblasts.", "Pflugers Arch.", 1999, pp. 239-244, vol. 438(3).

Capon, A., et al. , "Laser assisted skin closure (LASC) by using an 815-nm diode-laser system accelerates and improves wound healing. ", "Lasers Surg. Med.", 2001, pp. 168-175, vol. 28, No. 2.

Contag, C.H. and M.H. Bachmann , "Advances in in vivo bioluminescence imaging of gene expression.", "Annu. Rev. Biomed. Eng.", 2002, pp. 235-260, vol. 4.

Contag, C.H., et al., "Visualizing gene expression in living mammals using a bioluminescent reporter", "Photochem. Photobiol", 1997, pp. 523-531, vol. 66.

Currie, R.W., et al., "Heat-shock response is associated with enhanced postischemic ventricular recovery.", "Circulation Research", 1988, pp. 543-549, vol. 63.

Davidson, J.M., "Animal models for wound repair", "Arch. Dermatol. Res.", 1998, pp. S1-11, vol. 290 Suppl.

Desmettre, T., et al. , "Heat shock protein hyperexpression on chorioretinal layers after transpupillary thermotherapy.", "Invest. Ophthalmol. Vis. Sci.", 2001, pp. 2976-2980, vol. 42.

Diller, K.R., "Stress protein expression kinetics.", "Annu. Rev. Biomed. Eng.", 2006, pp. 403-424, vol. 8.

Dinh, H.K., et al., "Gene expression profiling of the response to thermal injury in human cells.", "Physiol Genomics", 2001, pp. 3-13, vol. 7.

Duncan, R.F. , "Inhibition of Hsp90 function delays and impairs recovery from heat shock.", "The FEBS Journal", 2005, pp. 5244-5256, vol. 272, No. 20.

El Sherif, A.F. et al., "Soft and hard tissue ablation with short-pulse high peak power and continuous thulium-silica fibre lasers", "Lasers in Medical Science", 2003, pp. 139-147, vol. 18.

Eldor, R., et al. , "New and experimental approaches to treatment of diabetic foot ulcers: a comprehensive review of emerging treatment strat", "Diabet. Med.", 2004, pp. 1161-1173, vol. 21(11).

Flanders, K.C., et al. , "Hyperthermia induces expression of transforming growth factor-beta s in rat cardiac cells in vitro and in vivo", 1993, pp. 404-410, vol. 92, Publisher: J. Clin. Invest.

Reliant Technologies, Inc. (Company), "Understanding Fraxel Laser Treatment. A Physician's Guide to Making Informed Purchasing Decisions", 2006, Publisher: Reliant Technologies, Inc.

Fried, N.M., et al., "High-Power Thulium Fiber Laser Ablation of Urinary Tissues at 1.94 um", "Journal of Endourology", Jan./Feb. 2005, pp. 25-31, vol. 19, No. 1.

Fried, N.M., "High-Power Laser Vaporization of the Canine Prostate Using a 110 W Thulium Fiber Laser at 1.91 mm", "Lasers in Surgery and Medicine", 2005, pp. 52-56, vol. 36.

Fried, Nathan M., "Thulium Fiber Laser Lithotripsy: An In Vitro Analysis of Stone Fragmentation Using a Modulated 110-Watt Thulium Fiber La", "Lasers in Surgery and Medicine", 2005, pp. 53-58, vol. 37.

Gabai, V.L., et al. , "Hsp70 prevents activation of stress kinases. A novel pathway of cellular thermotolerance.", "J. Biol. Chem.", 1997, pp. 18033-18037, vol. 272.

Geronemus, Roy G., "Fractional Photothermolysis: Current and Future Applications", "Lasers in Surgery and Medicine", 2006, pp. 169-176, vol. 38.

Gowda, A., et al. , "Cardioprotection by local heating: improved myocardial salvage after ischemia and reperfusion", "Ann. Thorac Surg.", 1998, pp. 1241-1247, vol. 65.

Hargitai, J., et al. , "Bimoclomol, a heat shock protein co-inducer, acts by the prolonged activation of heat shock factor-1.", "Biochem. Biophys. Res. Commun.", 2003, pp. 689-695, vol. 307, No. 3.

Hedelund, L., et al., "Ablative Versus Non-Ablative Treatment of Perioral Rhytides. A Randomized Controlled Trial With Long Term Blinded Clini", "Lasers in Surgery and Medicine", 2006, pp. 129-136, vol. 38.

Henriques, et al., "Studies of Thermal Injury", "Harvard Medical School", 1946.

Itzkan, I., et al., "The thermoelastic basis of short pulsed laser ablation of biological tissue", "Proc. National Academy of Sciences USA", 1995, pp. 1960-1964 , vol. 92.

Jaattela M., et al., "Major heat shock protein hsp70 protects tumor cells from tumor necrosis factor cytotoxicity.", "The EMBO Journal", 1992, pp. 3507-3512, vol. 11, No. 10.

Jacques, Steven L., "Laser-tissue interactions. Photochemical, photothermal, and photomechanical.", "Surgical Clinics of North America", Jun. 1992, pp. 531-558, vol. 72, No. 3.

Kabakov, A.E., et al. , "Stressful preconditioning and HSP70 overexpression attenuate proteotoxicity of cellular ATP depletion.", 2002, pp. C521-534, vol. 283, Publisher: Am. J. Physiol. Cell Physiol.

Kawalec, J.S., et al., "A review of lasers in healing diabetic ulcers", "The Foot", 2004, pp. 68-71, vol. 14.

Khan, Misbah Huzaira, et al., "Intradermally Focused Infrared Laser Pulses: Thermal Effects at Defined Tissue Depths", "Lasers in Surgery and Medicine", 2005, pp. 270-280, vol. 36.

Kim, D., et al., "Heat shock protein hsp70 accelerates the recovery of heat-shocked mammalian cells through its modulation of heat shock t", "Proc Natl Acad Sci U S A", 1995, pp. 2126-2130, vol. 92, No. 6.

Kim, J.M., et al. , "Effect of thermal preconditioning before excimer laser photoablation.", "J. Korean Med. Sci.", 2004, pp. 437-446, vol. 19.

Laubach, Hans-Joachim, et al., "Skin Response to Fractional Photothermolysis", "Lasers in Surgery and Medicine", 2006, pp. 142-149, vol. 38.

Lepore, D.A., et al., "Role of priming stresses and Hsp70 in protection from ischemia-reperfusion injury in cardiac and skeletal muscle. ", "Cell Stress Chaperones", 2001, pp. 93-96, vol. 6.

Manstein, Dieter, et al., "Fractional Photothermolysis: A New Concept for Cutaneous Remodeling Using Microscopic Patterns of Thermal Injury", "Lasers in Surgery and Medicine", 2004, pp. 426-438, vol. 34.

Merchant, et al., "Poloxamer 188 enhances functional recovery of lethally heat-shocked fibroblasts", "J Surg Res", 1998, pp. 131-140, vol. 74.

Nollen, E.A., et al. , "In vivo chaperone activity of heat shock protein 70 and thermotolerance.", 1999, pp. 2069-2079, vol. 19, No. 3.

O'Connell-Rodwell, C.E., et al. , "A genetic reporter of thermal stress defines physiologic zones over a defined temperature range.", "The FASEB Journal", 2004, pp. 264-271, vol. 18.

Oh, H.J., et al. , "Hsp110 protects heat-denatured proteins and confers cellular thermoresistance.", "J. Biol. Chem.", 1997, pp. 31636-31640, vol. 272, No. 50.

Parsell, et al., "The function of heat-shock proteins in stress tolerance: degradation and reactivation of damaged proteins", "Annu Rev Genet", 1993, pp. 437-496, vol. 27.

Pespeni, M., et al. , "In vivo stress preconditioning", "Methods", 2005, pp. 158-164, vol. 35.

Rylander, et al., "Heat shock protein expression and injury optimization for laser therapy design", "Lasers in Surgery and Medicine", 2007, pp. 731-746, vol. 39.

Rylander, M.N., et al., "Optimizing heat shock protein expression induced by prostate cancer laser therapy through predictive computational model", "J Biomed Opt", 2006, pp. 041113, vol. 11(4).

Seppa, L., et al. , "Upregulation of the Hsp104 chaperone at physiological temperature during recovery from thermal insult.", "J. Mol. Microbiol.", 2004, pp. 217-225, vol. 52.

Sherar, M.D., et al. , "Interstitial microwave thermal therapy for prostate cancer: method of treatment and results of a phase I/II trial.", "J. Urol.", 2001, pp. 1707-1714, vol. 166, No. 5.

Snoeckx, L.H., et al. , "Heat shock proteins and cardiovascular pathophysiology.", "Physiol Rev", 2001, pp. 1461-1497, vol. 81.

Souil, et al., "Treatment with 815-nm diode laser induces long-lasting expression of 72-kDa heat shock protein in normal rat skin.", "Br. J. Dermatol", 2001, pp. 260-266, vol. 144.

Thomsen, Sharon, "Pathologic analysis of photothermal and photomechanical effects of laser-tissue interactions.", "Photochem. Photobiol.", 1991, pp. 825-835, vol. 53, No. 6.

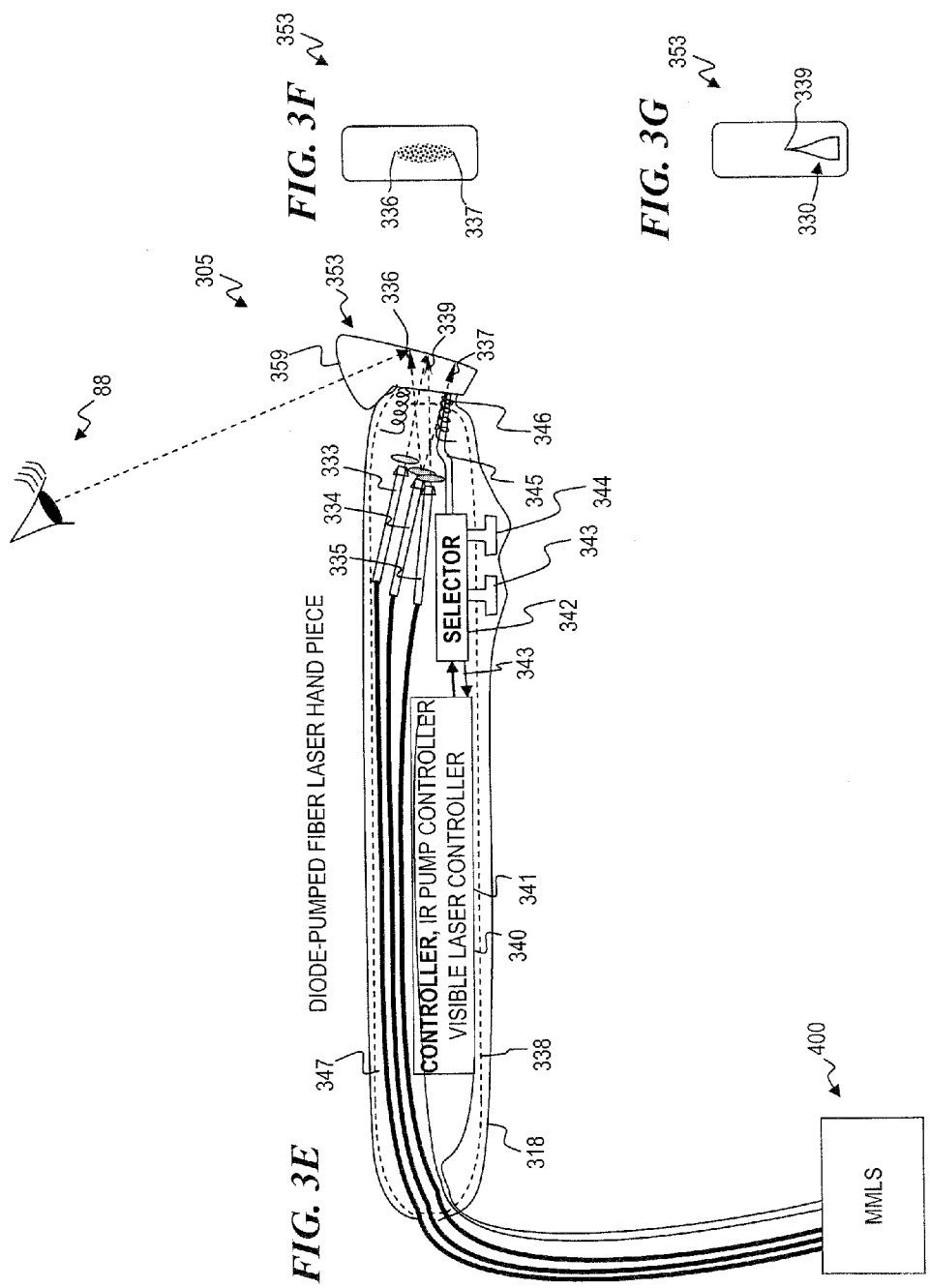

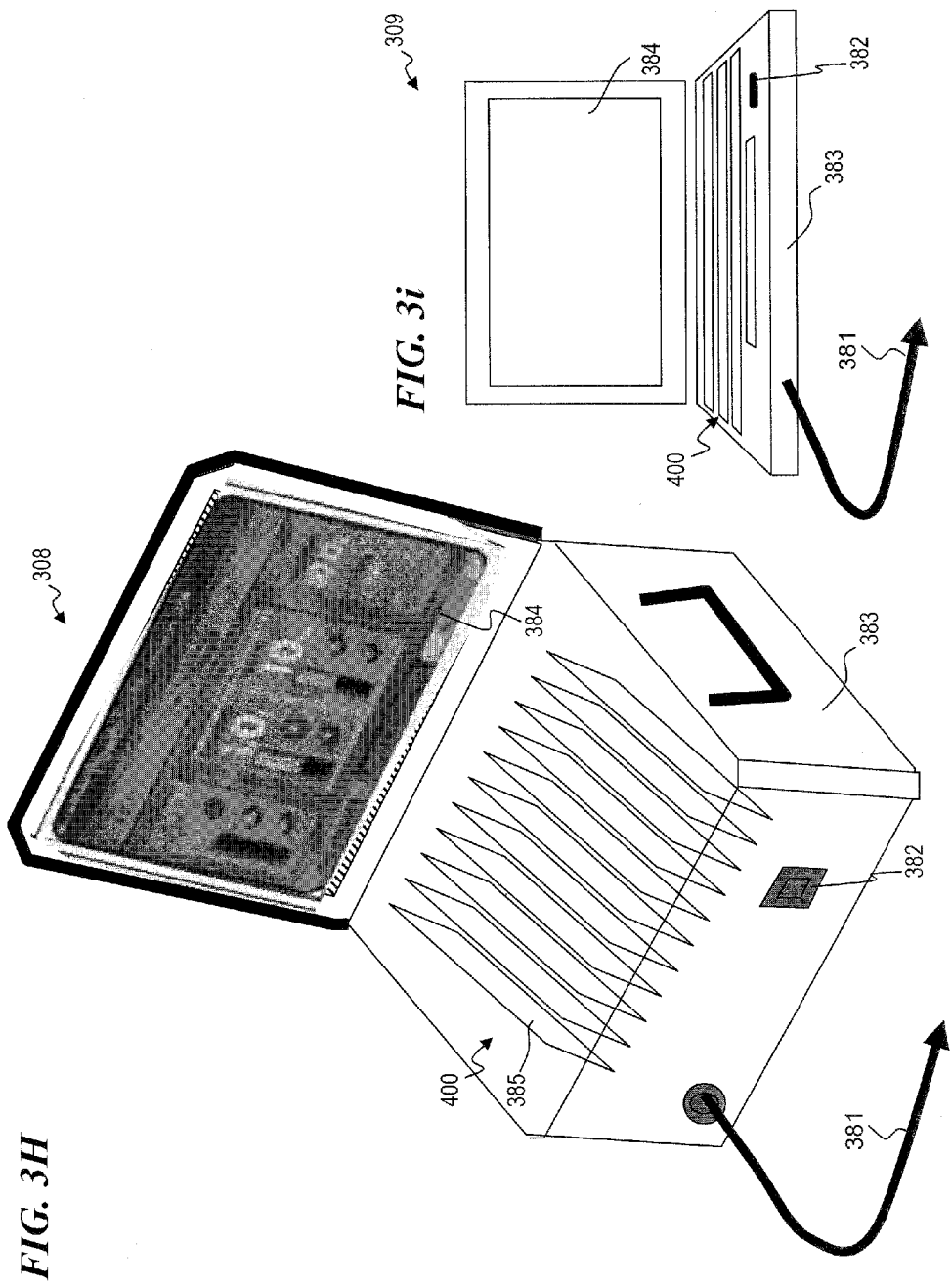

MULTIPLE-MODE DEVICE FOR HIGH-POWER SHORT-PULSE LASER ABLATION AND CW CAUTERIZATION OF BODILY TISSUES

CROSS-REFERENCE TO RELATED APPLICATIONS

This application is a divisional application of U.S. patent application Ser. No. 12/050,937 filed Mar. 18, 2008 and titled "METHOD AND MULTIPLE-MODE DEVICE FOR HIGH-POWER SHORT-PULSE LASER ABLATION AND CW CAUTERIZATION OF BODILY TISSUES" (which issued as U.S. Pat. No. 8,202,268 on Jun. 19, 2012), which claims benefit under 35 U.S.C. §119(e) of U.S. Provisional Patent Application No. 60/895,480 filed Mar. 18, 2007 and titled "DEVICE FOR HIGH-POWER PULSED-LASER ABLATION OF BODILY TISSUES," each of which is incorporated herein by reference in its entirety.

This invention is also related to U.S. patent application Ser. No. 11/257,793 filed Oct. 24, 2005 and titled "APPARATUS AND METHOD FOR OPTICAL STIMULATION OF NERVES AND OTHER ANIMAL TISSUE" (which issued as U.S. Pat. No. 7,736,382 on Jun. 15, 2010), U.S. patent application Ser. No. 11/536,639 filed Sep. 28, 2006 and titled "MINIATURE APPARATUS AND METHOD FOR OPTICAL STIMULATION OF NERVES AND OTHER ANIMAL TISSUE" (which issued as U.S. Pat. No. 7,988,688 on Aug. 2, 2011), U.S. Provisional Patent Application Ser. No. 60/872,930 filed Dec. 4, 2006 and titled "APPARATUS AND METHOD FOR CHARACTERIZING OPTICAL SOURCES USED WITH HUMAN AND ANIMAL TISSUES," U.S. patent application Ser. No. 11/536,642 filed Sep. 28, 2006 and titled "APPARATUS AND METHOD FOR STIMULATION OF NERVES AND AUTOMATED CONTROL OF SURGICAL INSTRUMENTS," U.S. Provisional Patent Application Ser. No. 60/884,619 filed Jan. 11, 2007 and titled "VESTIBULAR IMPLANT USING INFRARED NERVE STIMULATION," U.S. Provisional Patent Application Ser. No. 60/894,679 filed Mar. 13, 2007 and titled "FRACTIONAL PHOTOLYSIS USING A SUB-MICROSECOND PULSED FIBER LASER," and U.S. patent application Ser. No. 11/420,729 filed May 26, 2006 and titled "FIBER- OR ROD-BASED OPTICAL SOURCE FEATURING A LARGE-CORE, RARE-EARTH-DOPED PHOTONIC-CRYSTAL DEVICE FOR GENERATION OF HIGH-POWER PULSED RADIATION AND METHOD" (which issued as U.S. Pat. No. 7,391,561 on Jun. 24, 2008), each of which is incorporated herein in its entirety by reference.

FIELD OF THE INVENTION

The invention relates generally to tissue optics (interactions of light with human or other-animal tissue), and more particularly to methods and multiple-mode apparatus having a first mode that provides first mode for precision cutting that ablates tissue using a series of sub-microsecond sub-milli-Joule pulses to precisely cut, ablate, and/or destroy animal tissue (e.g., for urological or ear-nose-throat (ENT) procedures, as well as orthopedics, gastroenterology, and general surgery), and a second cauterization mode precision tissue ablation with a coagulation (i.e., hemostatic) function using laser output as continuous-wave (CW) and/or long pulses, wherein the second mode is configured to minimize heat damage to surrounding tissue, optionally using a thulium-doped fiber laser operating with a wavelength in the range of 1.9 to 2 microns.

BACKGROUND OF THE INVENTION

The current state of the art treatment for minimally invasive surgical applications requiring tissue cutting or removal relies on high-power laser pulses for precise tissue ablation. Currently the holmium-doped yttrium aluminum garnet (Ho:YAG) and potassium-titanyl-phosphate (KTP) (having a typical penetration depth of 350 µm) and carbon dioxide ($CO_2$) (having a typical penetration depth of 5 µm) lasers are used for a variety of procedures in urology, orthopedics, ENT, gastroenterology, and general surgery to address the wide range of surgical needs for high-power laser-ablation applications to enable faster, more efficient treatments and reduce operating and anesthesia time. Alternatively, the neodymium-doped yttrium aluminum garnet (Nd:YAG) laser has a deeper penetration (~2-3 mm) in soft tissues and is useful for coagulation. Applications specific to the Ho:YAG in urologic surgery involve the urethra (ablation, incision, tumor removal), bladder (bladder neck incisions, calculi, tumors, soft tissue ablation), ureter (calculi, incision, tumor removal), prostate (HoLAB, HoLEP, TVIP), kidney (calculi), and in some cases coagulation of blood. Clearly, the Ho:YAG laser has been adopted by the medical field due to the acceptable performance of the existing device and its ability to transmit through optical fibers.

An article authored by Nathanial M. Fried et al. titled "*High-power thulium fiber laser ablation of urological tissues at 1.94 µm*" (Journal of Endourology Vol. 19(1), pages 25-31, 2005) describes a 40 W thulium fiber laser operating at a wavelength of 1.94 µm delivered radiation in a continuous-wave or pulsed mode (10 milliseconds (msec)) through either 300-µm- or 600-µm-core low —OH silica fibers for vaporization of canine prostate and incision of animal ureter and bladder-neck tissues. The thulium fiber laser vaporized prostate tissue at a rate of 0.21±0.02 g/min. The thermal-coagulation zone measured 500 to 2000 µm (0.5 to 2 mm), demonstrating the potential for hemostasis. Laser incisions were also made in bladder tissue and ureter, with coagulation zones of 400 to 600 µm. They concluded that the thulium fiber laser has several potential advantages over the holmium laser, including smaller size, more efficient operation, more precise incision of tissues, and operation in either the pulsed or the continuous-wave mode. However, before clinical use will be possible, development of higher-power thulium fiber lasers and shorter pulse lengths will be necessary for rapid vaporization of the prostate and more precise incision of urethral/bladder-neck strictures, respectively. See also Fried, N. M., High-power laser vaporization of the canine prostate using a 110 W thulium fiber laser at 1.91 µm, *Lasers in Surgery and Medicine*, 36:52-56 (2005).

There are, however, several limitations associated with these current devices:

1. Insufficient control of the damage zone: These lasers can cause significant thermal damage during soft-tissue incision, with a minimal thermal damage zone of 400-500 µm or greater. This collateral thermal damage outside the irradiated tissue zone is undesirable for many procedures requiring precise ablation, such as ureteral strictures (abnormal narrowing of the lumen of a ureter, which causes functional obstruction) and urethral strictures (abnormal narrowing of the urethra) and bladder-neck contractures.

2. Non-ideal pulse structure: The pulse structure of the clinical Ho:YAG system is limited to pulse durations of 200 to 1000 μsec pulses (pulses that are too long to achieve stress-confined ablation), leaving this laser in a thermally confined regime which is not optimal for tissue cutting or perhaps coagulation.
3. Inefficient power requirements: The clinical Ho:YAG laser is inefficient at high-power operations and requires a 220-V source and large system hardware.
4. Inefficient fiber coupling efficiency: The clinical Ho:YAG laser-beam diameters are large and hard to focus into small optical fibers (those which are approximately 200-μm diameter), which complicates use in flexible ureteroscopes in the upper urinary tract.

U.S. Pat. No. 5,459,745 titled "TM:YALO, 1.94-MICRON, SOLID STATE LASER" was issued to Esterowitz et al., and is herby incorporated by reference. This patent describes a thulium-doped solid state laser capable of operation at a wavelength that has a shallow absorption depth in tissue. The laser included a laser cavity defined by first and second reflecting surfaces opposing each other on an optical axis, a thulium-doped YALO crystal disposed in the cavity, and a pump source for pumping the crystal with a pump beam at a preselected wavelength to enable the crystal to emit a most preferred 1.94 micron laser output. The thulium-doped YALO crystal is preferably an A-cut crystal. Such alignment of this material provides a reliable mode at 1.94 microns which has excellent tissue absorption characteristics for medical applications. The length l of the crystal, the concentration N of the dopant and the transmissivity T of the output coupler, which define an expression NlT, can be varied as long as the expression NlT produces a value which does not exceed about 0.32 centimeters.

An article authored by A. F. El-Sherif and T. A. King titled, "*Soft and hard tissue ablation with short-pulse high peak power and continuous thulium-silica fibre lasers*" (Lasers in Medical Science, Vol 18, pages 139-147, 2003) is incorporated herein by reference. The article describes investigating the use of thulium lasers operating near ~2 μm for various medical applications. The newly developed $Tm^{3+}$ silica fibre laser in Q-switched and CW operation was investigated to determine its efficiency in the interaction with soft and hard tissues. The interaction was investigated using a free-running continuous (CW) $Tm^{3+}$-doped fibre laser (wavelength 1.99 μm, with self-pulsation ranging over 1 to few tens of microseconds) and for novel Q-switched operation of the same fibre laser (pulse durations from 150 to 900 ns and pulse repetition rates from 100 Hz to 17 kHz). Residual damage and affected zones using the Q-switched laser were nearly six times smaller than using the CW fibre laser for about 50 s of exposure time, and increased with pulse repetition rate. The energy required to ablate tissue with the Q-switched fibre laser ranged from 0.2 to 0.6 $kJ/cm^3$ and was significantly smaller than that for the CW fibre laser of 153 to 334 $kJ/cm^3$. Under both high-resolution reflected optical microscopy and histological examination, tissue crater depths were observed as cleanly cut with smooth walls and minimal charring in the case of Q-switched operation of the fibre laser. This study is the first direct comparison of tissue interaction of short-pulse (Q-switched) and CW $Tm^{3+}$-doped silica fibre lasers on crater depth, heat of ablation and collateral damage. The Q-switched $Tm^{3+}$-doped silica fibre laser effectively ablates tissue with little secondary damage.

U.S. patent application Ser. No. 11/856,646, tiled "ELECTROSURGICAL APPARATUS AND METHODS FOR TREATMENT AND REMOVAL OF TISSUE" by Dahla, et al. is incorporated herein by reference. This patent application describes an apparatus and methods for ablating, severing, cutting, shrinking, coagulating, or otherwise modifying a target tissue to be treated. In a method for treating a target tissue, an active electrode of an electrosurgical probe is positioned in at least close proximity to the target tissue in the presence of an electrically conductive fluid. A high frequency voltage is then applied between the active electrode and a return electrode, wherein, the high frequency voltage is sufficient to volumetrically remove (ablate), sever, or modify at least a portion of the target tissue. The probe comprises a multi-lumen shaft having a plurality of internal lumens, and a return electrode coil oriented substantially parallel to the shaft distal end. The active electrode may be in the form of a metal disc, a hook, or an active electrode coil. In the latter embodiment, the active electrode coil is typically arranged substantially orthogonal to the return electrode coil. Methods of making an active electrode coil, a return electrode coil, and an electrosurgical probe are also disclosed.

U.S. patent application Ser. No. 11/747,663 titled "APPARATUS AND METHOD FOR ABLATION-RELATED DERMATOLOGICAL TREATMENT OF SELECTED TARGETS" by DeBenedictis; Leonard C., et al. is incorporated herein by reference. This patent application describes a treatment for skin containing selected targets that provides feedback in response to a measurement enabled by the ablation of holes. The inventive apparatus includes an electromagnetic source configured to emit ablative electromagnetic energy, a delivery system, a sensing element, and a controller. The delivery system can be configured to receive ablative energy from the electromagnetic source and deliver it to multiple discrete locations at the selected region to form a pattern of discrete holes in epidermal and dermal tissue of the skin. The lipid content a portion of the tissue can be evaluated using a sensing element. At least one pulse of electromagnetic energy is delivered to the skin under control of a controller in response to the result of a measurement by the sensing element. The apparatus may include a positional sensor to provide additional dosage control, particularly when the inventive method is used with a continuously movable handpiece.

U.S. Pat. No. 5,769,840 titled "MICROSURGERY USING ALTERNATING DISRUPTIVE AND THERMAL LASER BEAM PULSES" by Schirmer; Kurt E is incorporated herein by reference. This patent describes a method and an apparatus for conducting microsurgery on human or animal tissue which includes alternately providing an Argon laser beam pulse and a YAG laser beam pulse in a cycle which is equal to or less than one second. A robotic device including piston and cylinder arrangements is provided for activating the control keys on a control panel associated with the Argon and YAG lasers.

U.S. Pat. No. 5,656,186 titled, "METHOD FOR CONTROLLING CONFIGURATION OF LASER INDUCED BREAKDOWN AND ABLATION" by Mourou; Gerard A. et al. is incorporated herein by reference. This patent describes a method for laser induced breakdown of a material with a pulsed laser beam where the material is characterized by a relationship of fluence breakdown threshold ($F_{th}$) versus laser beam pulse width (T) that exhibits an abrupt, rapid, and distinct change or at least a clearly detectable and distinct change in slope at a predetermined laser pulse width value. The method comprises generating a beam of laser pulses in which each pulse has a pulse width equal to or less than the predetermined laser pulse width value. The beam is focused to a point at or beneath the surface of a material where laser induced breakdown is desired. The beam may be used in combination with a mask in the beam path. The beam or mask may be moved in the x, y, and z directions to produce desired features. The technique can produce features smaller than the spot size and Rayleigh range due to enhanced damage threshold accuracy in the short pulse regime.

U.S. Pat. No. 5,112,328 titled "METHOD AND APPARATUS FOR LASER SURGERY", by Taboada; John et al. is incorporated herein by reference. This patent describes an apparatus and method for laser surgery in which laser energy, pulsed or continuous, is focused to a focus spot of ten to thirty microns which is located within tissue, or the like to cause highly localized heating. The pulsed radiation is in the TEM (oo) mode, has a wavelength of approximately 1064 nanometer, the pulses being not in excess of 100 nanoseconds and the pulse rate being approximately 2000 per second. Where the laser beam is continuous or pulsed, it has a wavelength of approximately 1400 to 1800 nanometer, or in photoablative modes, having a wavelength of 190 to about 300 nanometers. The focus spot may be caused to move relative to the axis of a handpiece; and liquid may flow across the exposure site to remove debris. A handpiece may have an endoscope including a glass contact tip at its distal end to receive light and to acquire an image of the exposure site probes for eye surgery include a quartz rod in a sheath, the quartz rod having a beveled distal end surface through which the laser radiation is emitted and may have infusion and aspiration passages with ends coplanar with the beveled end surface of the quartz rod.

U.S. Pat. No. 6,096,031 titled, "HIGH REPETITION RATE ERBIUM: YAG LASER FOR TISSUE ABLATION" and U.S. Pat. No. 6,395,000 titled, "HIGH REPETITION RATE ERBIUM: YAG LASER FOR TISSUE ABLATION" both by Mitchell; Gerald M. et al. are incorporated herein by reference. These patents describe a medical laser system for ablating biological material. The system includes an Erbium: YAG gain medium capable of generating a pulsed output having a wavelength of 2.9 microns. The laser is optimized to generate a pulsed output having a repetition rate of at least 50 hertz and preferably at least 100 hertz. The output is delivered to the target tissue via an optical fiber. Preferably, a suction source is provided to aspirate the tissue as it is being ablated. The erbium laser system provides accurate ablation with minimal damage to surrounding tissue.

U.S. Pat. No. 6,529,543 titled "APPARATUS FOR CONTROLLING LASER PENETRATION DEPTH", by Anderson; R. Rox et al. is incorporated herein by reference. This patent describes systems and tools for controlling the optical penetration depth of laser energy, e.g., when delivering laser energy to target tissue in a patient. The systems and tools control the optical penetration depth (OPD) by controlling the incident angle at which the laser energy is delivered to the target area of the patient. Embodiments of the invention include an optical coupler that permit a user to vary the incident angle and thereby selectably control the OPD of incident laser energy. Fabricating the optical coupler to have a refractive index greater than that of the target tissue can enhance the range of selectable OPDs. The laser energy, which is delivered to the desired depth, can cause alteration of the target tissue by, e.g., heating, ablation, and/or photochemical reaction.

U.S. Pat. No. 6,310,900 tiled "LASER DIODE PACKAGE WITH HEAT SINK" by Stephens; Edward F. et al. is incorporated herein by reference. This patent describes a laser diode assembly including a laser diode having an emitting surface and a reflective surface opposing the emitting surface. Between the emitting and reflective surfaces, the laser diode has first and second surfaces to which a first heat sink and second heat sink are attached, respectively, via a solder bond. A spacer element is disposed between the first and second heat sinks and is below the laser diode. The spacer element has a width that is chosen to provide optimum spacing between the first and second heat sinks. The spacer element has a height that is chosen to place the emitting surface of the laser diodes at a position that is substantially flush with the upper surfaces of the heat sinks. A substrate is positioned below the first and second heat sinks and is attached to these two components usually via a solder bond. The substrate is preferably of a nonconductive material so that electrical current flows only through the heat sinks and the laser diode. To properly locate the spacer element, the substrate may include a locating channel into which the spacer element fits. Each of the heat sinks is coated with a solder layer prior to assembly. Once the components are placed in their basic assembly position, only one heating step is needed to cause the solder layer on the heat sinks to reflow and attach each heat sink to the adjacent laser diodes and also to the substrate.

U.S. Pat. No. 6,228,076 titled "SYSTEM AND METHOD FOR CONTROLLING TISSUE ABLATION" by Winston; Thomas R. et al. is incorporated herein by reference. This patent describes a control system and method for controlling tissue ablation uses optical time domain reflectometry data to differentiate abnormal tissue from normal tissue, and to control ablation of abnormal tissue by controlling a tissue ablative apparatus. Using data provided by an interferometric apparatus, the control system provides control signals to the tissue ablative apparatus, controlling activation of the tissue ablation apparatus so that normal tissue is left untreated while abnormal tissue is ablated.

U.S. Pat. No. 4,733,660 titled "LASER SYSTEM FOR PROVIDING TARGET SPECIFIC ENERGY DEPOSITION AND DAMAGE" by Itzkan; Irving is incorporated herein by reference. This patent decribes a hand piece for use with a laser includes a scanning mechanism which controls dosimetry of radiation applied to a target area which is adjustable to limit thermal diffusion from the light absorbing portion of the irradiated target site for selective target specific energy deposition. When used for dermatologic purposes, the adjustable scanning mechanism permits radiation to impinge on tissue for a predetermined period of time for the selective necrosis of highly-filled blood vessels, while leaving adjacent tissue and empty blood vessels undamaged. The dwell time of the laser beam is designed to match the diffusion time for thermal destruction of the wall of the abnormal vessel, with the dwell time adjusted by the scanning rate.

U.S. Patent Application Serial No 2002/0045811 titled "LASER ABLATION PROCESS AND APPARATUS" by Kittrell, Carter is incorporated herein by reference. This patent application describes a laser catheter wherein optical fibers carrying laser light are mounted in a catheter for insertion into an artery to provide controlled delivery of a laser beam for percutaneous intravascular laser treatment of atherosclerotic disease. A transparent protective shield is provided at the distal end of the catheter for mechanically displacing intravascular blood and protecting the fibers from the intravascular contents, as well as protecting the patient in the event of failure of the fiber optics. Multiple optical fibers allow the selection of tissue that is to be removed. A computer controlled system automatically aligns fibers with the laser and controls exposure time. Spectroscopic diagnostics determine what tissue is to be removed.

U.S. Pat. No. 5,897,549 titled "TRANSFORMATION OF UNWANTED TISSUE BY DEEP LASER HEATING OF WATER" and U.S. Pat. No. 6,083,217 titled "DESTRUCTION FOR UNWANTED TISSUE BY DEEP LASER HEATING OF WATER" by Tankovich are both incorporated herein by reference. These patents describe a process for treating relatively deep formations of undesirable sub-epidermal tissue by heating water in the formations with a laser to denature proteins therein. A laser beam is operated to irradiate a target region of highly vascularized dermal tissue or mechanically traumatized tissue in a blood-circulating living being, such as a human. The laser light preferably has a wavelength of about 1.45-1.68 microns (micrometers). This operating parameter provides the laser beam with a low enough water-absorption coefficient to facilitate adequate penetration into the target area while still providing enough energy to heat water to a temperature capable of spatially conforming vascularized tissue in the target area. Treatment pursuant to the above-cited patents may be applied to medical procedures applied to the skin to treat sub-epidermal tissues for a variety of aesthetic treatments. These include treatments for highly vascular regions of sub-epidermal tissue (such as strawberry hemangioma, spider veins, telangiectasia, Karposi's sarcoma, and the like), as well as regions of dermis collagen mechanically damaged due to various reasons (such as frequent muscular contraction, burning, traumatic irritation, worsening of mechanical damage due to environmental exposure, and the like), and aesthetic improvement of scars.

An article authored by Thomsen, Sharon titled "*Pathological Analysis of Photothermal and Photomechanical Effects of Laser-Tissue Interactions*" (Photochemistry and Photobiology, Vol. 53, No. 6, pages 825-835, 1991) is incorporated herein by reference. This article describes that pathologic analysis of the biologic effects and mechanisms of laser-tissue interactions requires correlation of the irradiation parameters with the biologic status and response of the target tissues over time. The photobiologic mechanisms of laser-induced tissue injury can be separated into three categories, photochemical, photothermal and photomechanical. Anatomic pathologic analysis of laser-induced lesions reveals alterations that represent either specific markers of the photobiologic mechanism or non-specific reactions to tissue injury. Repair, regeneration and wound healing of laser induced lesions appear to be non-specific responses to the type of tissue damage rather than the photobiologic mechanism producing the lesion.

An article authored by Jacques, Steven L. titled "*Laser-Tissue Interactions: Photochemical, Photothermal, and Photomechanical*" (Lasers in General Surgery, Vol. 72, No. 3, pages 531-558, 1992) is incorporated herein by reference. This article describes the variety of laser effects and how the characteristics of various lasers and various tissues allow different effects to occur. The authors approach the problem of laser-tissue interactions just like the novice, by turning up the laser power until something happens. However, in this article, they do not discuss thresholds but rather concentrate on what is going to happen.

An article authored by Manstein, Dieter et al. titled "*Fractional Photothermolysis: A New Concept for Cutaneous Remodeling Using Microscopic Patterns of Thermal Injury*" (Lasers in Surgery and Medicine, Volume 34, pages 426-438, 2004) is incorporated herein by reference. This article describes a new concept of skin treatment called fractional photothermolysis (FP), achieved by applying an array of microscopic treatment zones (MTZ) of thermal injury to the skin. Two prototype devices emitting at 1.5 µm wavelength provided a pattern of micro-exposures with variable MTZ density. Effects of different MTZ densities were tested on the forearms of 15 subjects. Clinical effects and histology were assessed up to 3 months after exposure. Treatment of photoaged skin on the periorbital area in an additional 30 subjects receiving four treatments over a period of 2-3 weeks was also tested. Tissue shrinkage and clinical effects were assessed up to 3 months after treatment. Pattern densities with spacing of 250 µm (microns) or more were well tolerated. Typical MTZ had a diameter of 100 µm and penetrated 300 µm into the skin. Reepithelialization was complete within one day. Clinical effects were assessed over a 3-month period. Histology at 3 months revealed enhanced undulating rete ridges and increased mucin deposition within the superficial dermis. Periorbital treatments were well tolerated with minimal erythema and edema. Linear shrinkage of 2.1% was measured 3 months after the last treatment. The wrinkle score improved 18% ($P<0.001$) three months after the last treatment. FP is a new concept for skin restoration treatment. Safety and efficacy were demonstrated with a prototype device. Further clinical studies are necessary to refine the optimum parameters and to explore further dermatological applications.

An article authored by Khan, Misbah Huzaira titled "*Intradermally Focused Infrared Laser Pulses Thermal Effects at Defined Tissue Depths*" (Lasers in Surgery and Medicine; Volume 36, pages 270-280, 2005) is incorporated herein by reference. This article describes a study to produce controlled, spatially confined thermal effects in dermis. A one-Watt, 1500-nm fiber-coupled diode laser was focused with a high numerical aperture (NA) objective to achieve a tight optical focus within the upper dermis of skin held in contact with a glass window. The delivery optics was moved using a computer-controlled translator to generate an array of individual exposure spots. Fresh human facial skin samples were exposed to a range of pulse energies at specific focal depths, and to a range of focal depths at constant pulse energy. Cellular damage was evaluated in frozen sections using nitro-blue tetrazolium chloride (NBTC), a lactate dehydrogenase (LDH) activity stain. Loss of birefringence due to thermal denaturation of collagen was evaluated using cross-polarized light microscopy. The extent of focal thermal injury was compared with a model for photon migration (Monte Carlo Simulation), heat diffusion, and protein denaturation (Arrhenius model). Arrays of confined, microscopic intradermal foci of thermal injury were created. At high NA, epidermal damage was avoided without active cooling. Foci of thermal injury were typically 50-150 µm (microns) in diameter, elliptical, and at controllable depths from 0 to 550 µm. Both LDH inactivation and extracellular matrix denaturation were achieved. Spatially confined foci of thermal effects can be achieved by focusing a low-power infrared laser into skin. Size, depth, and density of microscopic, thermal damage foci may be arbitrarily controlled while sparing surrounding tissue. This may offer a new approach for nonablative laser therapy of dermal disorders.

An article authored by Hedelund, L. et al. titled "*Ablative Versus Non-Ablative Treatment of Perioral Rhytides. A Randomized Controlled Trial With Long Term Blinded Clinical Evaluations and Non-Invasive Measurements*" (Lasers in Surgery and Medicine; Volume 38, pages 129-136, 2006) is incorporated herein by reference. This article describes a comparison of the efficacy and side effects of $CO_2$ laser resurfacing and intense pulsed light (IPL) rejuvenation for treatment of perioral rhytides. Twenty-seven female subjects with perioral rhytides (class I-III) were randomly treated with either $CO_2$ laser or IPL (three monthly treatments). Efficacy was evaluated by patient self-assessments and blinded photographs up to 12 months postoperatively. Side effects were assessed clinically. Non-invasive measurements included: trans-epidermal water loss (TEWL), skin reflectance, skin elasticity, and ultrasound. $CO_2$ laser resurfacing resulted in higher degrees of patient satisfaction and clinical rhytide reduction compared to IPL rejuvenation up to 12 months postoperatively (patient evaluations, $P<0.05$) (observer evaluations, P<0.008). Laser-induced side effects included erythema, dyspigmentation, and milia whereas no side effects were observed after IPL rejuvenation. Non-invasive measurements showed a significant higher reduction of the sub-epidermal low-echogenic band in $CO_2$ laser treated areas versus IPL treated areas (12 months postoperatively, P<0.001). Skin elasticity (expressed as Young's modulus) increased in both groups (P=ns). One month postoperatively a significant increase in TEWL values (P<0.009) and skin redness % (P<0.02) was found in $CO_2$ laser treated patients versus IPL treated patients. No significant differences were seen in skin pigmentation % during the observation period. $CO_2$ laser resurfacing induces a significantly higher degree of clinical rhytide reduction followed by considerably more side effects compared to IPL rejuvenation in a homogeneous group of patients.

An article authored by Laubach, Hans-Joachim et al. titled "*Skin Response to Fractional Photothermolysis*" (Lasers in Surgery and Medicine; Volume 38, pages 142-149, 2006) is incorporated herein by reference. This article describes Fractional photothermolysis (FP), a new concept using arrays of microscopic thermal damage patterns to stimulate a therapeutic response. They analyzed epidermal and dermal response to FP with the aim of correlating histological and clinical response. Twelve subjects received a single treatment with a prototype diode laser emitting at a wavelength of 1500 nm, delivering 5 mJ per microscopic treatment zone (MTZ), and a density of 1600 MTZs/$cm^2$ on the forearm. Biopsies were procured over a period of 3 months. The biopsies were analyzed by two blinded dermatopathologists using hematoxylin and eosin (Hematoxylin and Eosin Stain), Elastica von Gieson, nitro-blue-tetrazolium-chloride (NBTC) viability, and immunohistochemistry stains. Furthermore, the treatment sites were evaluated in vivo by confocal microscopy. Twenty-four hours after fractional photothermolysis, the continuity of the epidermal basal cell layer is restored. Complete epidermal regeneration is obtained seven days after the treatment. Microscopic epidermal necrotic debris (MENDs) areas are seen as early as one day after fractional photothermolysis. MENDs contain melanin pigment, and are shed from the epidermis within seven days. Evidence of increased collagen III production is shown with immunohistochemistry (IHC) staining seven days after FP. IHC for heat shock protein 70 (HSP 70) shows the expression of HSP one day after fractional photothermolysis, and IHC for alpha smooth muscle actin shows the presence of myofibroblasts seven days after fractional photothermolysis. These findings are concordant with the induction of a wound healing response by fractional photothermolysis. There is no evidence of residual dermal fibrosis 3 months after treatment. A single treatment with fractional photothermolysis induces a wound healing response in the dermis. A mechanism for the precise removal of epidermal melanin is described, in which MENDs act as a melanin shuttle.

An article authored by Geronemus, Roy G. titled "*Fractional Photothermolysis: Current and Future Applications*" (Lasers in Surgery and Medicine; Volume 38, pages 169-176, 2006) is incorporated herein by reference. This article describes an alternative treatment for dermatologic conditions called fractional photothermolysis (FP). FP produces arrays of microscopic thermal wounds called microscopic treatment zones (MTZs) at specific depths in the skin without injuring surrounding tissue. Wounding is not apparent because the stratum corneum remains intact during treatment and acts as a natural bandage. Downtime is minimal and erythema is mild, permitting patients to apply cosmetics immediately after treatment. As with other nonablative laser modalities, multiple treatments are required. FP represents an alternative for treatment of dermatologic conditions without the adverse effects of ablative laser devices and can be used on all parts of the body. FP can be used for the treatment of facial rhytides, acne scars, surgical scars, melasma, and photodamaged skin.

Physician operators can achieve a favorable cosmetic outcome in patients by "painting" or moving the continuous-motion Fraxel Laser Treatment (FLT) tip, over the contours of the face and neck in multiple strokes. The result is a uniform glow on the face, neck, hands, or any body location with minimal risk of uneven pigmentation due to occasional under-treatment or over-treatment. Fraxel laser operators control dosage levels with the aid of a high-speed, beam-deflecting system and an intelligent optical tracking system (IOTS), which features compensation for the natural variation in hand motion. It monitors hand speed and tip direction by responding to the microscopic features on the skin (highlighted by a blue tint applied prior to treatment). Treatment density (micro treatment zones (MTZs)/$cm^2$) level is maintained by the high-speed laser pattern generator built into the Fraxel handpiece. With the aid of patented beam-deflector technology, the Fraxel laser delivers up to 3000 precision pulses per second, more than 10 times the rate of conventional laser devices. The 15 mm treatment tip permits operators to cover up to 12 $cm^2$ (~2 $in^2$) per second with a single pass. With this feature, FLT operators can treat the entire face and neck in 25 minutes and can treat larger off-face areas such as the chest, aims and legs. With traditional laser handpieces, treatment patterns are produced at target sites by stamping. When treatment is applied to adjacent sites, however, imperfect handpiece alignment results in the appearance of unwanted zones of demarcation. Furthermore, multiple stamping passes are necessary with traditional handpieces to attain the desired treatment density (MTZs/$cm^2$) in a single treatment session. Multiple passes are excessively tedious and result in Moire artifacts. In addition, all treatment zones are laid down at the same time and bulk heating is avoided only by intense surface cooling at the expense of failure to coagulate the epidermis. Such treatment modalities, because they produce insufficient epidermal damage, cannot provide superficial resurfacing. In contrast, the Fraxel laser handpiece lays down individual MTZs sequentially in time, thus avoiding bulk heating and permitting more aggressive treatment of the epidermis and dermis. The randomized delivery also results in a macroscopically uniform treatment pattern. In addition, FLT's multi-pass technique allows the user to easily blend treatment zones and feather treatment edges.

U.S. patent application Ser. No. 11/747,711 titled "APPARATUS AND METHOD FOR A COMBINATION OF ABLATIVE AND NONABLATIVE DERMATOLOGICAL TREATMENT" by Leonard DeBenedictis et al. is incorporated herein by reference. This patent application describes a treatment for skin wherein a pattern of holes is ablated in a selected region of skin tissue using an optical source. Substantially nonablative energy is delivered to the selected region to at least two holes in the pattern to thermally heat a target in or just beneath the skin, such as hair follicles, sebaceous glands, or subcutaneous fat. The invention may further be improved by adding a feedback mechanism that adapts the nonablative energy in response to a measurement enabled by the ablation of holes. The apparatus may include a positional sensor to provide additional dosage control, particularly when the inventive method is used with a continuously movable handpiece.

U.S. patent application Ser. No. 11/749,066 titled "METHOD AND APPARATUS FOR FRACTIONAL LIGHT-BASED TREATMENT OF OBSTRUCTIVE SLEEP APNEA" by Leonard DeBenedictis et al. is incorporated herein by reference. This patent application describes an apparatus and method that uses fractional light based treatment to shrink soft tissue in the mouth or throat to reduce obstruction of the airways for patients suffering from obstructive sleep apnea. A light delivery probe with scanning optics can be used to deliver treatment. Cooling systems can be added to reduce damage to epithelial layers of tissue. Light based treatment can be nonablative or ablative and is preferably performed with a laser.

U.S. patent application Ser. No. 11/747,663 titled "APPARATUS AND METHOD FOR ABLATION-RELATED DERMATOLOGICAL TREATMENT OF SELECTED TARGETS" by Leonard DeBenedictis et al. is incorporated herein by reference. This patent application describes a treatment for skin containing selected targets that provides feedback in response to a measurement enabled by the ablation of holes. The inventive apparatus includes an electromagnetic source configured to emit ablative electromagnetic energy, a delivery system, a sensing element, and a controller. The delivery system can be configured to receive ablative energy from the electromagnetic source and deliver it to multiple discrete locations at the selected region to form a pattern of discrete holes in epidermal and dermal tissue of the skin. The lipid content a portion of the tissue can be evaluated using a sensing element. At least one pulse of electromagnetic energy is delivered to the skin under control of a controller in response to the result of a measurement by the sensing element. The apparatus may include a positional sensor to provide additional dosage control, particularly when the inventive method is used with a continuously movable handpiece.

U.S. Pat. No. 5,546,214 titled "METHOD AND APPARATUS FOR TREATING A SURFACE WITH A SCANNING LASER BEAM HAVING AN IMPROVED INTENSITY CROSS-SECTION" by Michael Black is incorporated herein by reference. This patent describes a method and apparatus for laser treatment of surfaces, such as tissue. In a preferred embodiment, the invention employs a unique reflective optical delivery system which produces an improved beam intensity cross-section which reduces thermal injury, increases the precision of the tissue interaction and allows the creation of craters with decreased sizes. Reflective optics provide precise, single-layer vaporization at low power levels without thermal injury to the underlying papillary dermis. Movable optical elements focus and direct the laser beam in a scanning pattern to treat a large area of the surface.

U.S. Pat. No. 5,151,098 titled "APPARATUS FOR CONTROLLED TISSUE ABLATION" by Hanspeter Loertscher; is incorporated herein by reference. This patent describes an apparatus for performing controlled tissue ablation in endolaser microsurgery, the apparatus including a laser delivery system coupled to a probe capable of transmitting the laser power through a suitable medium such as sapphire. The probe may include a central canal for aspiration and irrigation and delivers a cross-sectionally homogeneous power distribution. The apparatus is designed to control the ablation depth and to limit the zone of thermal damage in the remaining tissue.

U.S. Pat. No. 5,071,417 titled "LASER FUSION OF BIOLOGICAL MATERIALS" by Edward L. Sinofsky et al. is incorporated herein by reference. This patent describes an apparatus and methods for laser fusion of biological structures are disclosed employing a laser for delivery of a beam of laser radiation to an anastomotic site, together with a reflectance sensor for measuring light reflected from the site and a controller for monitoring changes in the reflectance of the light of the site and controlling the laser in response to the reflectance changes. In one embodiment, the laser radiation is delivered through a hand-held instrument via an optical fiber. The instrument can also include one or more additional fibers for the delivery of illumination light (which can be broadband or white light or radiation from a laser diode) which is reflected and monitored by the reflectance sensor. Reflectance changes during the course of the fusion operation at one or more wavelengths can be monitored (or compared) to provide an indication of the degree of tissue crosslinking and determine when an optimal state of fusion has occurred.

U.S. patent application Ser. No. 11/637,400 titled "SYSTEM AND METHOD FOR POINTING A LASER BEAM" by Steven Tidwell is incorporated herein by reference. This patent application describes an apparatus and method for directing a laser beam at an object. Some embodiments include generating direction-control information, based on the direction-control information, directing laser energy into a first fiber at a first end of a first fiber bundle during a first time period, forming an output beam of the laser energy from the second end of the first fiber bundle, and steering the output beam of the laser energy from the first fiber in a first selected direction of a plurality of directions during the first time period, and optionally modulating an intensity of the laser energy according to a predetermined pattern. The direction-control information is based on sensing electromagnetic radiation from a scene. Some embodiments use a remote camera wire-connected to the image processor to obtain scene information, while other embodiments use a second fiber bundle to convey image information from an external remote lens to a local camera.

U.S. Pat. No. 6,997,923 titled "METHOD AND APPARATUS FOR EMR TREATMENT", U.S. patent application Ser. No. 11/235,697 titled "METHOD AND APPARATUS FOR EMR TREATMENT" and U.S. patent application Ser. No. 11/599,786 titled "METHOD AND APPARATUS FOR EMR TREATMENT" all by R. Rox Anderson et al., are incorporated herein by reference. This patent and these patent applications describe a method and apparatus for performing a therapeutic treatment on a patient's skin by concentrating applied radiation of at least one selected wavelength at a plurality of selected, three-dimensionally located, treatment portions, which treatment portions are within non-treatment portions. The ratio of treatment portions to the total volume may vary from 0.1% to 90%, but is preferably less than 50%. Various techniques, including wavelength, may be utilized to control the depth to which radiation is concentrated and suitable optical systems may be provided to concentrate applied radiation in parallel or in series for selected combinations of one or more treatment portions.

U.S. Pat. No. 7,292,232 titled "DATA INPUT DEVICES AND METHODS FOR DETECTING MOVEMENT OF A TRACKING SURFACE BY A LASER SPECKLE PATTERN" by Craig Ranta et al. is incorporated herein by reference. This patent describes a data input device for use with an optically rough tracking surface comprising a substantially coherent light source for projecting a substantially coherent light beam onto the tracking surface for scattering the substantially coherent light beam. An optic guides the projected substantially coherent light beam toward the tracking surface and comprises a first boundary facing the substantially coherent light source and a second boundary opposite the first boundary. A detector detects at least a portion of the scattered light beam comprising a speckle pattern. The optic is arranged such that the tracking surface is spaced from the second boundary by a distance sufficient to inhibit any substantial retro-reflection of the substantially coherent light beam striking the second boundary from striking the detector.

A controller responsive to the detector operates the device in a tracking mode for utilizing the detected speckle pattern to track relative movement between the device and the tracking surface. The device is particularly useful in handheld and laptop devices, such as personal digital assistants, cellular phones, laptop computers, etc., where it is desirable to interact with a tracking surface comprising human skin, such as a fingertip.

In some embodiments, the Ranta patent provides an apparatus that includes a first fiber bundle having a plurality of light-transmitting fibers including a first fiber, a second fiber, and a third fiber, the first fiber bundle having a first end and a second end, a laser that emits laser energy, a processor that generates direction-control information, a fiber selector that is operatively coupled to the processor and based on the direction-control information, is configured to direct the laser energy into the first fiber at the first end of the first fiber bundle during a first time period, and transform optics located to receive the laser energy from the second end of the first fiber bundle and configured to form an output beam of the laser energy from the first fiber in a first selected direction of a plurality of directions during the first time period. Some embodiments further include a modulator that modulates an intensity of the laser energy according to a predetermined pattern. Some embodiments further include a sensor operatively coupled to receive electromagnetic radiation from a scene and to transmit sense information to the processor based on the received electromagnetic radiation, and wherein the processor is configured to generate the direction-control information based on the sense information. Some embodiments further include an ability to sense more than one object and simultaneously direct a plurality of laser beams in a plurality of different directions or sequentially direct a single laser beam in the plurality of different directions one at a time.

As used herein, a photothermolysis device is defined as any device that provides optical energy to cause dissociation, protein denaturation, or decomposition of animal tissue by heat. Conventional ablative laser technology causes heat damage to tissues surrounding the ablative site. There is a risk of infection and other side effects as a result. Conventional non-ablative-laser treatments provide less dramatic results. Fractional photothermolysis attempts to obtain the benefits of the two approaches described above.

There is a need for improved methods and apparatus for precision laser surgery. There is also a need for battery-powered, light-weight, portable laser surgery instruments. There is further a need for a plurality of modes of operation, including a cutting mode, a cauterizing mode, a fractional photolysis mode and/or the like.

SUMMARY OF THE INVENTION

In some embodiments, the present invention provides an apparatus and process having a plurality of modes of operation at least some of which share a fiber laser and/or fiber amplifier that is used to provide laser power for the plurality of modes of operation, including a cutting mode (e.g., by forming an overlapping, contiguous, or near contiguous series of micropores along a line to be cut), a cauterizing mode, a fractional photolysis mode and/or the like. In some embodiments, the apparatus is battery-powered, portable, and lightweight enough to be easily carried by a physician during use (e.g., having a computer-battery-laser portion that can be hung from a belt around the physicians waist, placed in a vest pocket, strapped to the physician's arm, or the like, and a light-delivery portion that can, for example, be held in the hand like a scalpel or pen). In some embodiments, a small rechargeable and/or replaceable battery of a type similar to that used in laptop computers is packaged together with the other heavy and/or bulky portions (e.g., semiconductor lasers used to obtain pump light, optically pumped fiber laser(s) and/or amplifier(s) used to receive the pump light and to generate and/or amplify the therapeutic laser light wavelength (also called the signal wavelength), electronic power supplies and conditioners to supply electrical power to the semiconductor pump lasers, controller and safety circuits used to control the types and timing of the signal-laser output for the various modes of operation), which are then connected via optical fiber to the handpiece used by the surgeon to perform the cutting, cauterizing, or other therapeutic operations. In some embodiments, the therapeutic laser light is of an infrared wavelength (e.g., between 1.9 and 2 micron wavelength), so visible light is also generated and delivered by optical fiber to the site of the operation to indicate the mode of operation and/or indicate the location to which the therapeutic laser light will be delivered (i.e., emitting a visible laser beam of a first color (or quality (such as pulsating in intensity)) to indicate that the therapeutic laser light is "off" and that when the therapeutic laser light is turned on, where the cutting/cauterizing will occur, and emitting a visible laser beam of a second color (or quality (such as outputting constant intensity)) to indicate that the therapeutic laser light is "on" and that the cutting/cauterizing is occurring.

In some embodiments, the plurality of modes includes a cutting mode that includes cutting to a substantially predetermined depth (e.g., by forming an overlapping, contiguous, or near contiguous series of micropores along a line to be cut). In some embodiments, the pulse energy and duration are controlled such that each micropore is of substantially the same depth (e.g., 0.05 mm deep, 0.1 mm deep, 0.25 mm deep, 0.5 mm deep, 1 mm deep, 1.5 mm deep, 2 mm deep, 2.5 mm deep, or other suitable depth) in order that the incision has a uniform depth per pass, such that the cut is not made too deep (which would endanger underlying tissues). If a deeper cut is desired, the surgeon can easily trace over the first cut with one or more additional passes in cutting mode to make that cut deeper. In some embodiments, the pulse energy and pulse duration are adjusted (e.g., in some embodiments, both are made smaller) in order to reduce the cut depth. In some embodiments, overlapping and/or contiguous micropores are formed along a line traced out by the surgeon while the surgeon presses an activation button correlated to the cutting function. In some embodiments, the speed at which the cutting tip is moved relative to the skin surface is measured and the timing between pulses is adjusted, in order to space the micropores from one another by the desired amount for the amount of overlap or amount of space. In some embodiments, the laser pulses are 15 to 180 nanoseconds (ns) in duration, and 50 to 200 microJoules (µJ) in energy.

In some embodiments, the initial pulses generate relatively shallow micropores, and as the tissue heats up, the cutting depth increases. In some embodiments, the initial pulses are given additional energy relative to latter pulses, in order that the cutting depth is constant for the length of the cut. In other embodiments, a constant energy is provided to each pulse, such that the start of a cut will be shallower than later portions.

In some embodiments, the plurality of modes includes a cauterizing and/or coagulation mode that includes heating a surface (such as walls of a previously formed cut formed by another mode of the instrument) to a substantially predetermined depth (e.g., by applying a series of longer pulses or quasi-CW signal). In some embodiments, the laser power and delivery-tip de-focusing optics are controlled or chosen such that the coagulation depth and temperature of each area is of substantially the same depth (or wall thickness) and same temperature (e.g., 0.10 mm (100 microns) deep, 100 degrees C., in some embodiments of a coagulation mode) in order that the cauterizing and/or coagulation has a uniform depth per pass, such that the heating is not made too deep (which would endanger underlying tissues). If further cauterizing and/or coagulation is desired, the surgeon can easily trace over the first pass with one or more additional passes in cauterizing and/or coagulation mode to make that cauterizing and/or coagulation deeper. In some embodiments, the laser power and pulse duration are adjusted (e.g., in some embodiments, both are made smaller) in order to reduce the cauterizing and/or coagulation depth. In some embodiments, the laser output power is approximately four watts CW for one-tenth second spread over an area of 10 square mm (e.g., a beam spot of 1 mm by 10 mm (0.1 $cm^2$) when moved across the surface at 2 cm per second) when in coagulation mode. In some embodiments, the laser output power is approximately two watts CW for one second spread over an area of 100 square mm (1 $cm^2$) when in coagulation mode. In some embodiments, the laser is operated in a quasi-CW pulsed mode wherein pump power is applied whenever output is desired (with no Q-switching used).

In some embodiments, the plurality of modes includes a fractional photolysis mode that includes forming a pattern of spaced-apart micropores to a substantially predetermined depth (e.g., by forming an overlapping, contiguous, or near contiguous series of micropores along a line to be cut). In some embodiments, the pulse energy and duration are controlled such that each micropore is of substantially the same depth (e.g., 0.5 mm deep, 1 mm deep, 1.5 mm deep, 2 mm deep, 2.5 mm deep, or other suitable depth) in order that the incision has a uniform depth per pass, such that the cut is not made too deep (which would endanger underlying tissues). If a deeper cut is desired, the surgeon can easily trace over the first cut with one or more additional passes in cutting mode to make that cut deeper. In some embodiments, the pulse energy and pulse duration are adjusted (e.g., in some embodiments, both are made smaller) in order to reduce the cut depth. In some embodiments, overlapping and/or contiguous micropores are formed along a line traced out by the surgeon while the surgeon presses an activation button correlated to the cutting function. In some embodiments, the speed at which the cutting tip is moved relative to the skin surface is measured and the timing between pulses is adjusted, in order to space the micropores from one another by the desired amount for the amount of overlap or amount of space. In some embodiments, the laser pulses are 15 to 180 nanoseconds (ns) in duration, and 50 to 200 microJoules (µJ) in energy In some embodiments, overlapping and/or contiguous micropores are formed along a line traced out by the surgeon while the surgeon presses an activation button correlated to the cutting function. In some embodiments, the speed at which the cutting tip is moved relative to the skin surface is measured and the timing between pulses is adjusted, in order to space the micropores from one another by the desired amount for the amount of overlap or amount of space between micropores (which are adjacent or overlapping when in cutting mode). In other embodiments, the pulse repetition rate (PRR) is set to one of the fixed PRRs (i.e., PRRs that are set to the desired rate and do not vary with the speed of the instrument relative to the surface of the tissue being treated).

In some embodiments, the present invention provides an apparatus and process wherein a high-power, pulsed thulium laser outputs infrared laser pulses delivered through an optical fiber, for cutting and ablating biological tissue. In some embodiments, the pulse duration is shortened sufficiently to keep inside the stress-confined ablation region of operation. In some embodiments, the pulse is shortened to near the stress-confined ablation region of operation, while, in some embodiments, being slightly in the thermal-constrained region of operation (in order to obtain a controlled-thickness wall of thermal coagulation or cauterization, e.g., in some such embodiments, the wall thickness of this thermal zone is between about 50 microns and 200 microns). In some embodiments, the laser is coupled to a small low —OH optical fiber (~100 µm diameter). In some embodiments, the device has a pulse duration of about 100 ns for efficient ablation; however, in some embodiments this parameter is adjustable. In some embodiments, the pulse length is adjustable to a first mode of operation in or near the stress-confined region of operation to cut or remove tissue with little or no collateral heat damage to surrounding tissue, and/or to a second mode of operation in or near the thermal-confined region of operation to coagulate blood to stop or prevent bleeding in surrounding tissue and/or to kill tissue surrounding the irradiated zone without (or while minimizing) the risk of surrounding tissue becoming dislodged (e.g., to prevent possible spread of cancerous cells to other parts of the body). In some embodiments, the pulse repetition rate (PRR) is adjustable from one or more single pulses to 50-kHz repeated pulses (in some embodiments, the PRR is variable up to 100 KHz). In some embodiments, the laser has a tunable pulse energy output (i.e., non-zero pulses) up to 50 mJ as output from the delivery fiber.

In some embodiments, the present invention is used to more precisely cut and/or destroy tissue (e.g., in the human body), while reducing or minimizing collateral heat damage to surrounding tissue. Uses for such cutting and/or destroying of tissue include procedures in the urethra (ablation, incision, tumor removal), bladder (bladder neck incisions, calculi, tumors, soft tissue ablation), ureter (calculi, incision, tumor removal), prostate (HoLAB, HoLEP, TVIP), kidney (calculi), and in some cases coagulation of blood. In other embodiments, the device is used for applications specific to ENT; including but not limited to procedures in larynx (benign laryngeal and vocal cord lesions, stenosis, cancer of the larynx and pharynx), oro-pharynx (LAUP, tonsillectomy, oral lesions), naso-pharynx (rhinophymo, septal surgery), otology (stapedontomy, laser assisted myringotomy, acoustic neuroma), and dermal (tumor resection or ablation). In yet other embodiments, the device is used for applications specific to gastroenterology; including but not limited to procedures for ablation, vaporization, incision, excision, and coagulation (gall bladder and bile duct stones, partial nephrectomy, appendectromy, neoplasms, cholecystectomy, hemorrhoidectomy, or polypectomy). In still other embodiments, the device is used for applications specific to orthopedics including but not limited to procedures in the contouring articular surfaces, chondroplasty, plica removal, lateral retinacular release, ligament and tendon release, meniscectomy, osteoarthritic lesion removal, synovectomy.

In other embodiments, the short-pulse thulium-fiber laser of the present invention is used for skin-resurfacing procedures such as described in U.S. Provisional Patent Application Ser. No. 60/894,679 filed Mar. 13, 2007 and entitled "FRACTIONAL PHOTOLYSIS USING A SUB-MICROSECOND PULSED FIBER LASER," and U.S. patent application Ser. No. 12/077,083 filed Mar. 13, 2008 and entitled "FRACTIONAL PHOTOLYSIS USING SUB-MICROSECOND PULSED FIBER LASER(S)," which are incorporated herein by reference. The patent application describes an apparatus and method using short pulses to induce wound-healing response from very localized laser ablation or mechanical trauma with minimal thermal tissue damage and reduced thermal protein denaturation. In some embodiments, the laser-pulse characteristics are chosen to obtain a desired tissue-penetration depth and to meet the stress-confinement criteria to achieve the desired photomechanical tissue trauma that induces the desired wound healing with minimal histological damage to neighboring cells. In some embodiments, the pulse duration is between about 2 ns and about 6 ns, the tissue-penetration depth is between about 1.8 mm and about 2.2 mm, a spot diameter is between about 0.15 mm and about 0.2 mm, a per-pulse energy is less than about 100 microJoules (µJ), and a laser wavelength is about 1550 nm. The laser energy used is significantly less than conventional methods of fractional photothermolysis (which typically use five milliJoules (5 mJ) or more per pulse).

In some embodiments, the short-pulse thulium laser of the present invention is used using the operational parameters shown in FIG. 2 of the present application (which is similar to FIG. 1 of that provisional patent application 60/894,679 and FIG. 1K of the non-provisional patent application 12/nnn, nnn).

Other advantages with the thulium fiber laser besides more efficient ablation include a smaller size and greater power efficiency than the current technologies. In some embodiments, the present invention provides a battery-powered surgical/coagulation device that is readily portable and usable in harsh environments such as on a battlefield. In some embodiments, the present invention provides a battery-powered multiple-mode surgical cutting and/or coagulation device that is readily portable and usable in harsh environments such as on a battlefield.

BRIEF DESCRIPTION OF THE DRAWINGS

FIG. 3E is a schematic diagram, partially in cross section, of a portable system 305 according to some embodiments of the invention.

FIG. 3F is a schematic diagram, of an end view of delivery optic face 353 of a portable system 305 according to some embodiments of the invention.

FIG. 3G is a schematic diagram, of an end view of delivery optic face 353, of a portable system 305 according to some embodiments of the invention.

FIG. 3H is a schematic perspective diagram of a portable system 308 according to some embodiments of the invention.

FIG. 3i is a schematic perspective diagram of a portable system 309 according to some embodiments of the invention.

DETAILED DESCRIPTION

Figure 1A:
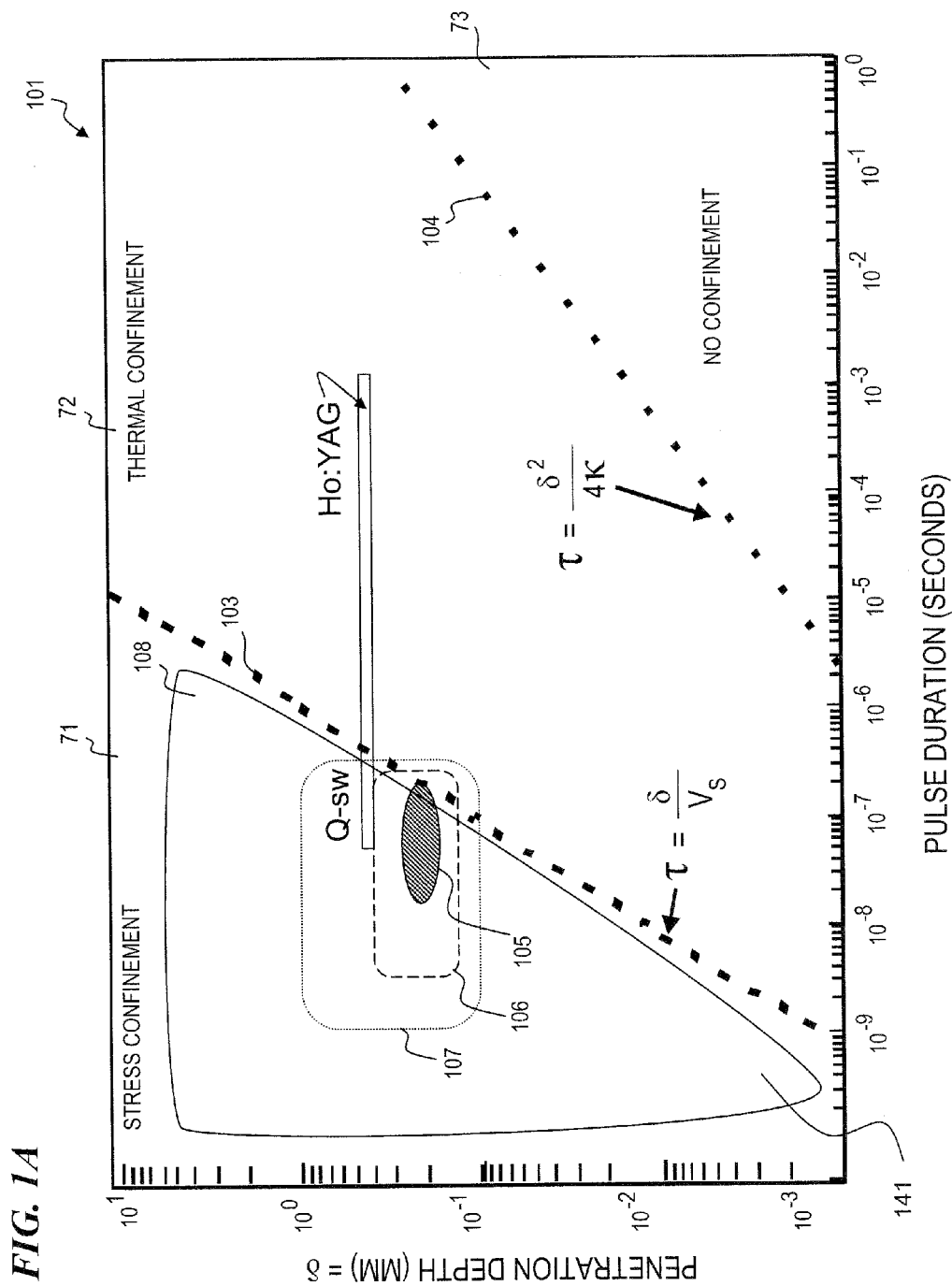
FIG. 1A is a graph 101 of tissue-penetration depth as a function of pulse duration, wherein three laser-tissue-interaction regions are defined: stress confinement, thermal confinement, or no confinement.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple figures. Signals and connections may be referred to by the same reference number or label, and the actual meaning will be clear from its use in the context of the description.

In some embodiments, the present invention provides an apparatus and process wherein a high-power, pulsed thulium laser outputs infrared laser pulses delivered through an optical fiber, for cutting and ablating biological tissue. In some embodiments, the thulium laser includes a thulium fiber laser. In some embodiments, the thulium laser includes a thulium crystal laser (such as one including a thulium-yttrium aluminate crystal such as described in U.S. Pat. No. 5,459,745 titled "TM:YALO, 1.94-MICRON, SOLID STATE LASER" issued to Esterowitz et al., which is herby incorporated by reference). In some embodiments, the laser is coupled to a small low —OH optical fiber (~100 µm diameter). (Optical fibers having very low hydroxyl (—OH) content are used for visible and near-infrared (near-IR) applications. The optical attenuation characteristics are quite different for high —OH and low —OH optical fiber core material. The —OH content of the core's fused silica must be formulated into the raw boule material before the optical fiber is made. The choice is dependent on the user's application. The low —OH type optical fiber has very low attenuation throughout the near-IR wavelength range from 700 nm to beyond 1800 nm, except for a small peak at 1385 nm, while high —OH optical fiber is used for ultraviolet wavelengths.) In some embodiments, the device has a pulse duration of about 100 ns for efficient ablation; however, in some embodiments this parameter is adjustable. In some embodiments, the repetition rate is adjustable from single pulses to 50 kHz. In some embodiments, the laser has an adjustable pulse energy output up to 50 mJ as output from the delivery fiber.

In some embodiments, the device described herein overcomes the limitations imposed by current laser technology in the medical applications described using the Ho:YAG or KTP laser, or using conventional thulium fiber lasers. One significant advantage of the short-pulse thulium fiber laser over existing lasers is the photobiological process by which this fiber laser targets. The Ho:YAG and KTP lasers fall in a thermally confined regime (see FIG. 1A), which implies that ablation is mediated by large temperature transients created in tissue, which will lead to thermal diffusion of heat to surrounding tissue zones lying outside and adjacent to the target area (the target area is the irradiated zone, which is equal to the spot size times the laser-penetration depth). This thermal diffusion leads to collateral damage and thus less precise destruction of tissue. While existing lasers are limited by relatively long pulse durations, the significantly shorter pulse from the short-pulse thulium fiber laser of the present invention falls in the stress-confined zone. Here, the thermal transients induced in tissue are minimized, which leads to more efficient and more precise tissue ablation because tissue damage is confined to the irradiated zone of tissue without thermal diffusion destroying adjacent tissue structures.

The precision of the thulium laser device is further increased over the existing architecture using a Ho:YAG laser, since the technology described here has a much smaller attainable irradiation zone in tissue. The irradiated zone in tissue depends on the spot size of the laser and the laser-penetration depth. The penetration depth of the thulium fiber laser is roughly two-to-three times less than that of the Ho:YAG laser (see FIG. 1A), since the thulium wavelength is tuned to match a water-absorption peak at 1.94 µm. The thulium-laser light can be coupled to a much smaller spot more efficiently than existing medical lasers. Thus, the minimum spot size attainable for tissue ablation is significantly enhanced with the thulium laser (roughly ½ the diameter of conventional Ho:YAG laser spots). Therefore, the total reduction in irradiated zone (and thus, the total increase in spatial precision of ablation) is theoretically on the order of one full order of magnitude (about 8-to-12 times). Experiments comparing the irradiated zone of a Ho:YAG versus a thulium laser of the present invention show that the zone of tissue necrosis was three (3) times smaller with the latter laser. (See: Vogel, A., Schmidt, P. and Fluke, B. *Minimization of thermomechanical side effects and increase of ablation efficiency in IR ablation by use of multiply Q-switched laser pulses*, Proc. SPIE Vol. 4617, p. 105-111, Laser Tissue Interaction XIII: Photochemical, Photothermal, and Photomechanical, Steven L. Jacques; Donald D. Duncan; Sean J. Kirkpatrick; Andres Kriete; Eds., 2002. They describe that large thermal damage zones have been observed after application of free-running holmium laser pulses inside the human body, as, for example, for arthroscopic surgery. The aim of their study was to reduce thermal damage by increasing the ablation efficiency, and to achieve a smooth surface of the ablated tissue. For that purpose they used a multiply Q-switched thulium laser ((lambda) equals 2.0 micrometers, acousto-optical QS) that emits pulse series consisting of a pre-pulse of 40-mJ energy and up to 6 ablation pulses of 100 mJ each, separated by time intervals of 60 microsecond(s). Q-switched laser pulses explosively ablated the target material. In a liquid environment, this led to the formation of cavitation bubbles and to mechanical damage of the surrounding tissue. The pre-pulse of 40 mJ served to minimize the cavitation effects, as it produced a small cavity that was then filled by the ablation products created by the burst of 100-mJ pulses. The pre-pulse created a channel between fiber tip and target that reduced absorption losses in the liquid. Reduction of cavitation effects and channel formation were demonstrated by time-resolved photography. The use of a thulium laser instead of a holmium laser contributed to the desired reduction of thermal damage, because the penetration depth of the thulium laser light in cartilage (approximately 170 micrometers) is only half as large as with the holmium laser.)

In some embodiments, the thulium laser is pumped by laser light from a pump laser that emits the pump laser beam at about 795 nm to pump the thulium fiber or crystal laser. In some embodiments, the pump laser includes a GaAlAs laser diode array or a GaAlAs laser diode. However, in other embodiments, the pump laser can also be a titanium sapphire laser which can also produce a continuous-wave (CW) or pulsed pump beam. In some embodiments, the pump wavelength of about 795 nm is used because 795 nm is within the absorption peak of the thulium in the solid-state (i.e., crystal or fiber) laser as discussed in U.S. Pat. No. 5,459,745 described above. In various embodiments, any pump source having a wavelength of about 793 nm to about 796 nm, or about 808 nm, is used.

In some embodiments, the present invention provides a sequence of sub-microsecond optical (e.g., laser) pulses configured to form a series of superheated microscopic columns of thermal damage in animal tissue (e.g., human tissue). In some embodiments, the series of superheated microscopic columns creates ablation or shock-wave tearing of the tissue that was irradiated, but a small total amount of heat is induced, thereby minimizing the heat dissipation to surrounding tissue, and reducing collateral heat damage to that surrounding tissue. In some embodiments, the series of columns is formed along a line, wherein the columns are contiguous to one another to form a continuous cut through a portion of the tissue. In some embodiments, additional series of contiguous columns, each series along a respective line, are formed over time to deepen a previous cut, or to excise a volume of tissue, or to destroy a volume of tissue without removing the destroyed tissue or heat-damaging the surrounding tissue.

In some embodiments, the present invention provides better selectivity of micropore creation by inducing a stress wave (i.e., stress-confinement-facilitated micropore creation) with minimal temperature increases (substantially no thermal confinement) and therefore the present invention reduces the heating of the irradiated tissue and thus reduces the thermal diffusion to surrounding non-irradiated tissue.

In some embodiments, the laser beam can be optimized or adjusted in beam spot size (e.g., in some embodiments, 0.15-mm to 0.2-mm spot diameter measured at full-width half-maximum (FWHM); while in other embodiments, the present invention provides spot diameters of about 0.01 to 0.02 mm, about 0.02 to 0.05 mm, about 0.05 to 0.1 mm, about 0.1 to 0.15 mm, about 0.2 to 0.25 mm, about 0.25 to 0.3 mm, about 0.3 to 0.35 mm, about 0.35 to 0.4 mm, about 0.4 to 0.45 mm, about 0.45 to 0.5 mm, about 0.5 to 0.55 mm, about 0.55 to 0.6 mm, about 0.6 to 0.65 mm, about 0.65 to 0.7 mm, about 0.7 to 0.8 mm, about 0.8 to 0.9 mm, or about 0.9 to 1 mm) that achieves the desired ablation result while minimizing collateral heat damage.

In some embodiments, the laser beam can be optimized or adjusted in terms of pulse energy (e.g., about 100 microJoules or less, in some embodiments; while in other embodiments, the present invention provides per-pulse energies of about 0.1-0.2 µJ, about 0.2-0.5 µJ, about 0.5-1 µJ, about 1-2 µJ, about 2-5 µJ, about 5-10 µJ, about 10-20 µJ, about 20-50 µJ, about 50-100 µJ, about 100-200 µJ, about 200-500 µJ, or about 500-1000 µJ) that achieves the desired ablation result while minimizing collateral heat damage.

In some embodiments, the laser beam can then be optimized or adjusted to have a short pulse duration (e.g., about 2 ns to 6 ns, in some embodiments; while in other embodiments, the present invention provides pulse lengths of about 0.1-0.2 ns, about 0.2-0.5 ns, about 0.5-1 ns, about 1-2 ns, about 2-3 ns, about 3-4 ns, about 4-6 ns, about 6-8 ns, about 8-10 ns, about 10-20 ns, about 20-30 ns, about 30-40 ns, about 40-60 ns, about 60-80 ns, about 80-100 ns, about 100-200 ns, about 200-300 ns, about 300-400 ns, about 400-600 ns, about 600-800 ns, or about 800-1000 ns) to achieve the desired photomechanical tissue trauma (e.g., in some embodiments, a tissue-penetration depth of about 1.8-2.2 mm; while in other embodiments, the present invention provides tissue-penetration depth of less than about 0.2 mm, or about 0.2-0.5 mm, about 0.5-0.8 mm, about 0.8-1.1 mm, about 1.1-1.4 mm, about 1.4-1.8 mm, about 2.2-2.6 mm, about 2.6-3 mm, about 3-3.5 mm, about 3.5-4 mm, about 4-4.5 mm, about 4.5-5 mm, about 5-6 mm, about 6-7 mm, about 7-8 mm, about 8-9 mm, about 9-10 mm, or greater than about 10 mm) that achieves the desired ablation result while minimizing collateral heat damage.

In some embodiments, the present invention uses a laser (e.g., one using a master-oscillator power-amplifier configuration) having an amplifying optical fiber having one or more optical waveguides (e.g., fibers having cores (longitudinal waveguides) defined by increased index of refraction (as are typical of conventional optical fibers and light-transmission fibers) or photonic-crystal structures (cores defined typically by longitudinal holes arranged in a pattern to define a core that can be either solid (e.g., doped with one or more rare earth elements) or hollow (used for high-power applications and not obtainable using increased index or refraction structures)), and various pumping and pulse-forming configurations, all of which are described in the commonly assigned U.S. patent application Ser. No. 11/420,729 titled "FIBER-OR ROD-BASED OPTICAL SOURCE FEATURING A LARGE-CORE, RARE-EARTH-DOPED PHOTONIC-CRYSTAL DEVICE FOR GENERATION OF HIGH-POWER PULSED RADIATION AND METHOD" filed May 26, 2006 by Fabio Di Teodoro et al., which is incorporated herein by reference, and which issued as U.S. Pat. No. 7,391,561 on Jun. 24, 2008. In some embodiments, the fiber is similar to those described, but the doping species is changed to be thulium or to include thulium. In some embodiments, the lasing wavelength is selected to be about 1.94 microns to obtain good absorption by water in the tissue being ablated. In other embodiments, a wavelength between about 1.9 microns and about 2.0 microns is chosen.

In other embodiments, the invention outputs a wavelength of about 4 microns, and, to obtain this desired wavelength, includes an optical parametric oscillator (OPO) such as that described in commonly assigned U.S. patent application Ser. No. 11/484,358 filed Jul. 10, 2006 by Angus Henderson and titled "APPARATUS AND METHOD FOR PUMPING AND OPERATING OPTICAL PARAMETRIC OSCILLATORS USING DFB FIBER LASERS," which is incorporated herein by reference, and which issued as U.S. Pat. No. 7,620,077 on Nov. 17, 2009.

In some embodiments, the laser pulse characteristics are chosen to obtain a desired tissue-penetration depth and to meet the stress-confinement criteria and thus, in some embodiments, the pulse duration is between about 2 ns and about 6 ns, the tissue-penetration depth is between about 1.8 mm and about 2.2 mm, a spot diameter is between about 0.15 mm and about 0.2 mm, a per-pulse energy is less than about 100 µJ and a laser wavelength is about 1550 nm. The literature suggests that the histological damage zone to neighboring cells is minimal with pulse parameters selected such that the stress-confinement-criteria are fulfilled when compared to use of thermally confined lasers. (See: Jacques, S. L., "Laser-tissue interactions. Photochemical, photothermal, and photomechanical." *Surg. Clin. North Am.*, 1992. 72(3): p. 531-58; Thomsen, S., "Pathologic analysis of photothermal and photomechanical effects of laser-tissue interactions." *Photochem. Photobiol.*, 1991. 53(6): p. 825-35; and Vogel, A., Venugopalan, V. "Mechanisms of pulsed laser ablation of biological tissues." *Chem. Rev.*, 2003. 103(5):577-644.)

FIG. 1A is a graph of tissue-penetration depth as a function of pulse duration, wherein three laser-tissue-interaction regions are defined: stress confinement, thermal confinement, or no confinement. The graph shows various laser-confinement zones in soft biological tissue (i.e., skin) based on the relationship between pulse duration and penetration depth. The small shaded/cross-hatched oval indicates the stress confined regime that the short-pulse thulium-fiber laser (SPTFL) occupies (e.g., using pulses between about 20 nanoseconds (nsec) and about 200 nanoseconds, and cutting about 0.2 mm deep, in some embodiments). In other embodiments, the operational parameters of the SPTFL are within the dashed rounded rectangle (e.g., using pulses between about 5 nanoseconds and about 300 nanoseconds, and cutting about 0.15 to 0.4 mm deep, in some embodiments). In yet other embodiments, the operational parameters of the SPTFL are within the dotted rounded rectangle (e.g., using pulses between about 1 nanoseconds and about 400 nanoseconds, and cutting about 0.1 to 1 mm deep, in some embodiments).

FIG. 1A is a graph 101 of the various laser confinement zones in soft biological tissue (i.e. skin) based on the relationship between pulse duration and penetration depth wherein the penetration depth for the cutting applications of the present invention is based on a typical range for human skin (0.05 mm to 3 mm). FIG. 1A shows three laser-tissue-interaction confinement-zone regions plotted against tissue penetration depth and pulse duration, wherein the three defined regions are: stress confinement 71, thermal confinement 72 or no confinement 73. The three laser-confinement zones in soft biological tissue (e.g., skin) are based on the relationship between the duration of the laser pulse (the horizontal axis) and its penetration depth in the tissue (the vertical axis). In some embodiments the small cross-hatched oval 105 indicates a region of pulse duration ranges versus penetration depth ranges used by one preferred embodiment of the short-pulse thulium laser system of the present invention. In other embodiments, the dashed rectangle 106 represents yet another region of pulse durations ranging from 3 nanoseconds (ns) to 200 ns, and a penetration depth ranging between about 0.15 mm to about 0.5 mm. In still other embodiments, the dotted rectangle 107 represents yet another region of pulse durations ranging from 1 nanoseconds (ns) to 300 ns, and a penetration depth ranging between about 0.1 mm to about 1 mm. In some embodiments, the larger rounded triangle 141 indicates still another stress-confined regime used. In some embodiments, the entire area above and to the left of the $\tau=\delta/V_S$ markings (the stress confinement region) indicate still another stress-confined pulses regime.

For FIG. 1A, the effective irradiated zone (the size of the micropore) is a volume of tissue (e.g., a cylinder of tissue in some embodiments) exposed to an effective photon flux sufficient to cause ablation with substantially no collateral thermal damage. The shape and diameter of the volume or cylinder is dependent upon the numeric aperture (NA) of the output optics and the laser spot diameter. In some embodiments, a low NA fiber is used in order to avoid the cost and size of an output lens. For laser beams having a small NA (e.g., an NA of less than about 0.12), the volume will be substantially cylindrical and can be achieved using a low NA fiber without additional optics. The length of the cylinder along its axis (i.e., its depth of penetration) is the depth within the tissue at which the radiant photon flux (number of photons per unit area) is reduced to a value of approximately 1/e (approximately 0.37) times the flux at the surface of the tissue. The diameter of the cylinder is the FWHM width across the laser spot. In some embodiments, the micropore (cylinder) is approximately 2 mm deep and approximately 0.2 mm in diameter.

Figure 1B:
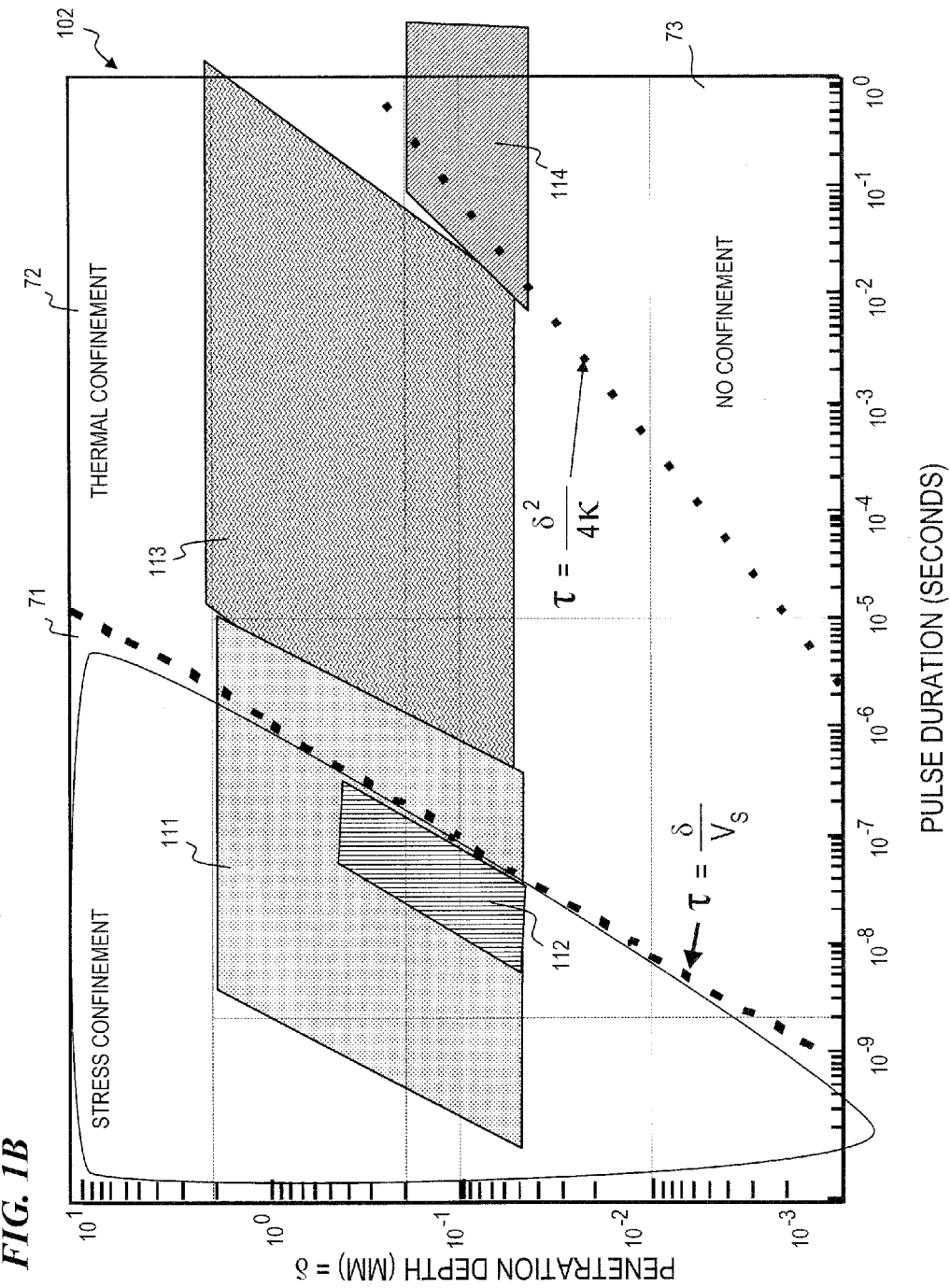
FIG. 1B is a graph 102 of the various laser confinement zones in soft biological tissue (i.e. skin) based on the relationship between pulse duration and penetration depth wherein the penetration depth for the cutting applications of the present invention is based on a typical range for human skin (0.05 mm to 3 mm).

For FIG. 1B, the formula $\tau=\delta/V_s$ (wherein $\tau$ is the pulse duration, $\delta$ is the penetration depth, and $V_s$ is the speed of sound in the tissue) has sometimes been denoted as $T=\delta/V_s$ and the formula $\tau=\delta^2/4\kappa$ has sometimes been denoted as $T=\delta^2/4\kappa$, without change in meaning.

FIG. 1B is a graph 102 of the various laser confinement zones in soft biological tissue (i.e. skin) based on the relationship between pulse duration and penetration depth wherein the penetration depth for the cutting applications of the present invention is based on a typical range for human skin (0.05 mm to 3 mm). FIG. 1B again shows three laser-tissue-interaction confinement-zone regions plotted against tissue penetration depth and pulse duration, wherein the three defined regions are: stress confinement 71, thermal confinement 72 or no confinement 73. In some embodiments the small vertical-line cross-hatched parallelogram 112 indicates a region of pulse duration ranges (about 10 ns to about 400 ns) versus penetration depth ranges (about 0.05 mm to about 0.5 mm deep cuts) used by one preferred embodiment, wherein the pulses are configured to cause stress-confined micropores with substantially no thermal damage (i.e., no coagulation effects or other heat-induced damage, which is useful when cutting bone or tendon tissue where coagulation is not needed and heat is to be avoided to the extent possible). In some embodiments the stippled parallelogram 111 indicates a region of pulse duration ranges (about 0.2 ns to about 10,000 ns) versus penetration depth ranges (about 0.05 mm to about 2 mm deep cuts) used by one preferred embodiment, wherein the pulses are configured to cause stress-confined micropores with substantially no thermal damage when in the stress-confinement region 71 (i.e., no coagulation effects or other heat-induced damage), and wherein the pulses are configured to cause primarily stress-confined micropores with slight heating (thermal damage) in the surrounding tissue when in the thermal-confinement region 72 (i.e., some coagulation effects or other heat-induced damage to surrounding tissue, useful for cutting and stopping minor bleeding from capillaries). In some embodiments the wavy-line cross-hatched parallelogram 113 indicates a region of pulse duration ranges (about 100 ns to about 1 second) versus penetration depth ranges (about 0.05 mm to about 2 mm deep ablations) used by one preferred embodiment, wherein the pulses are configured to cause thermal-confined micropores with substantial thermal damage when in the thermal-confinement region 72 (i.e., substantial coagulation effects or other heat-induced damage to surrounding tissue, useful for ablating large tissue volumes). In some embodiments the diagonal-line cross-hatched parallelogram 114 indicates a region of continuous wave (CW) or quasi-CW pulse-duration ranges (about 10 ms to about 1 second or more) versus penetration depth ranges (about 0.05 mm to about 0.2 mm deep coagulation results) used by one preferred embodiment, wherein the diffused CW laser energy is configured to cause substantial coagulation effects or other heat-induced damage to surrounding tissue, useful for homeostasis (quenching bleeding that may have been caused by the cutting mode).

Figure 2:
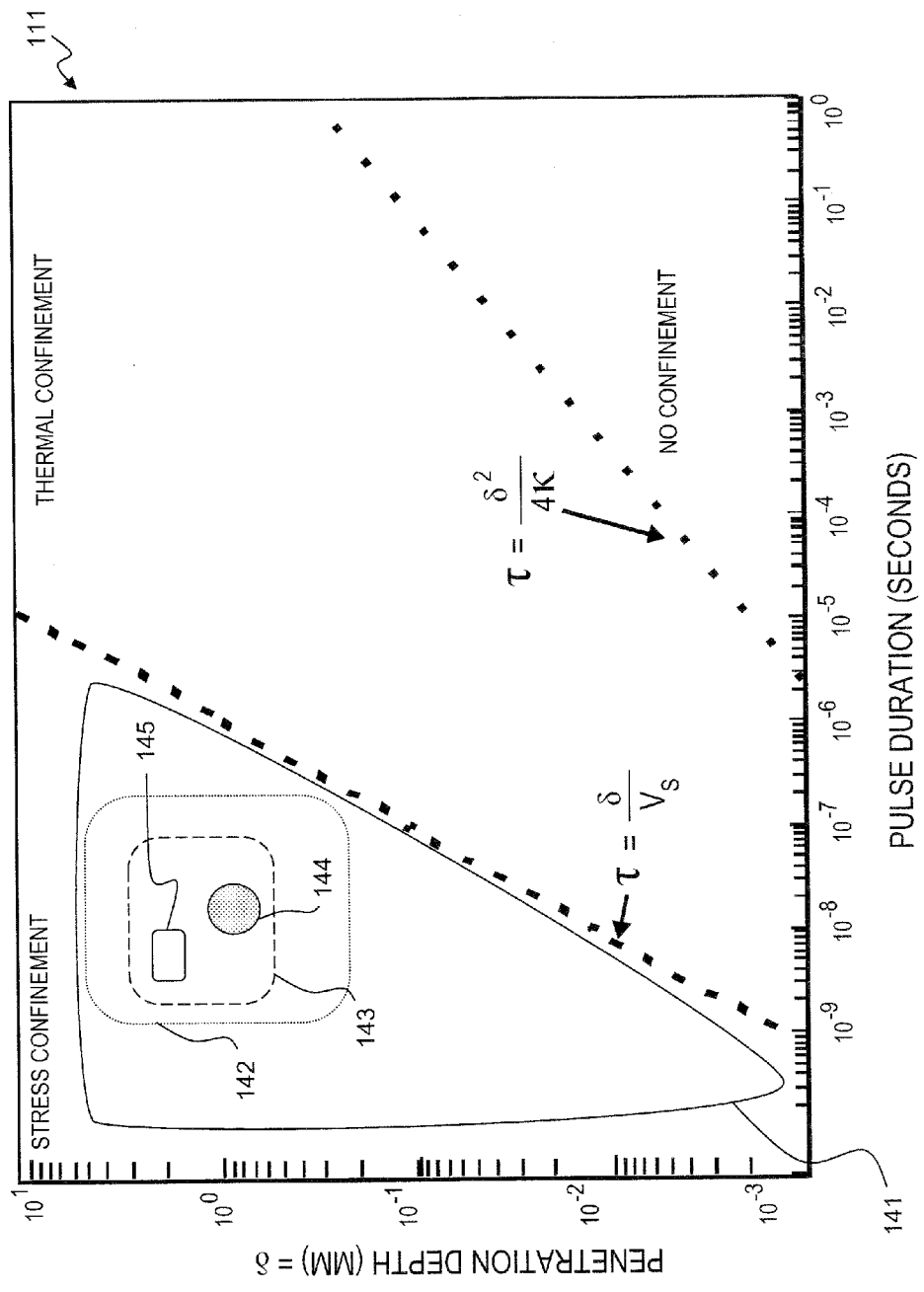
FIG. 2 is a graph 111 of tissue-penetration depth versus pulse duration, wherein three laser-tissue-interaction regions are defined: stress confinement, thermal confinement, or no confinement. The graph shows various laser-confinement zones in soft biological tissue (i.e., skin) based on the relationship between pulse duration and penetration depth. The filled circle indicates the stress-confined regime obtained by the nano-pulsed fiber laser (NPFL) of the present invention.

FIG. 2 is a graph 111 of tissue-penetration depth as a function of pulse duration, wherein the three laser-tissue-interaction regions are again defined: stress confinement, thermal confinement, or no confinement, wherein the various laser confinement zones in soft biological tissue (i.e., skin) based on the relationship between pulse duration and penetration depth. In some embodiments: the small stippled circle 144 indicates one stress-confined regime that the nanosecond-pulsed fiber laser (NPFL) system operation occupies (e.g., using pulses between about 5 nanoseconds and about 10 nanoseconds, and cutting about 0.5 to 1 mm deep, in some embodiments). In some embodiments, the small rounded rectangle 145 indicates another stress-confined regime used (i.e., 2-6 ns pulses, 1.8-2.2 mm deep). In some embodiments, the medium dashed rounded rectangle 143 indicates yet another stress-confined regime used. In some embodiments, the large dotted rounded rectangle 142 indicates still another stress-confined regime used. In some embodiments, the larger rounded triangle 141 indicates still another stress-confined regime used. In some embodiments, the entire area above and to the left of the $\tau=\delta/V_S$ markings (the stress confinement region) indicate still another stress-confined pulses regime. The graph 111 shows various laser-confinement zones in soft biological tissue (i.e., skin) based on the relationship between pulse duration and penetration depth. The regions in FIG. 2 all represent cutting modes (generation of a series of contiguous or overlapping micropores that together form a cut along a line, where the cut has the predefined cutting depth equal to the depth of the micropores) with substantially no thermal damage.

Figure 3B:
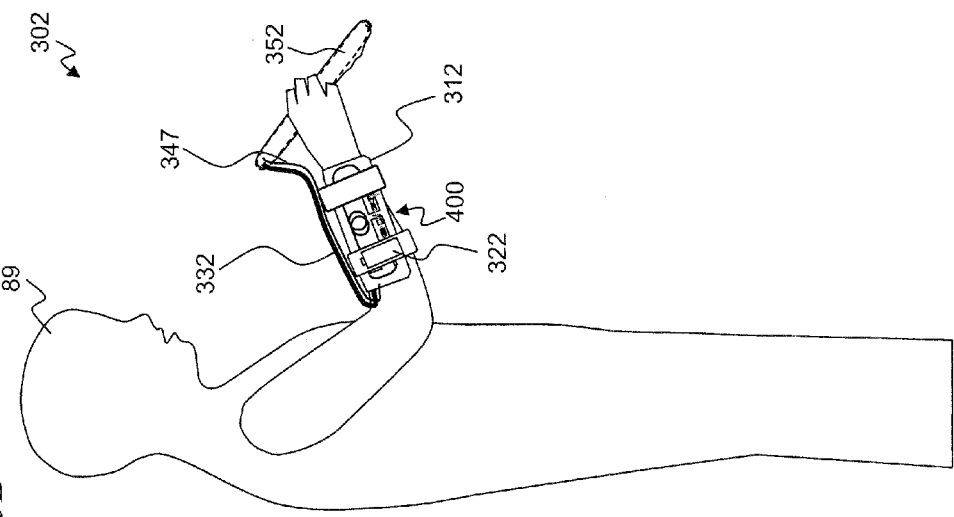
FIG. 3B is a schematic diagram, partially in cross section, of a portable system 302 according to some embodiments of the invention.
Figure 3A:
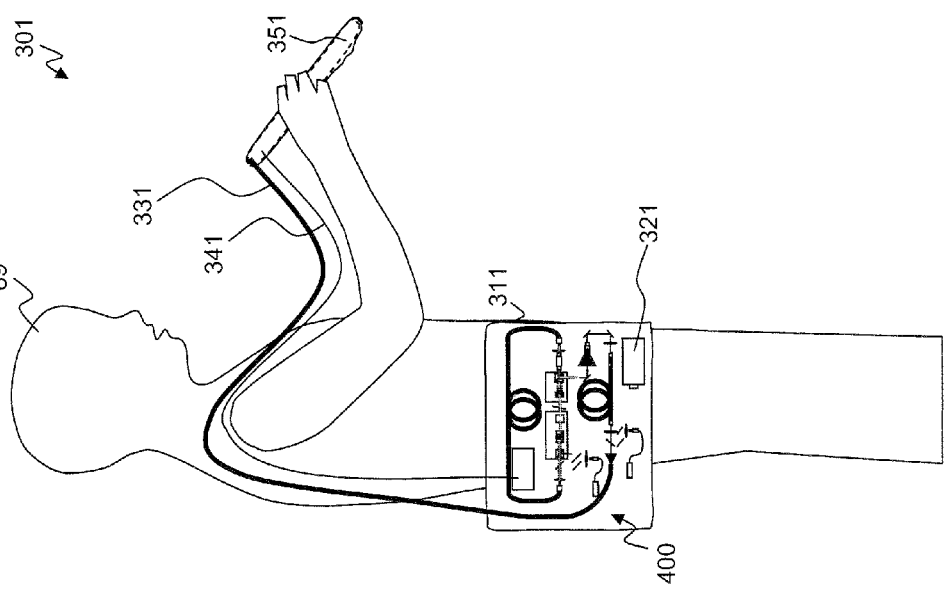
FIG. 3A is a schematic diagram, partially in cross section, of a portable system 301 according to some embodiments of the invention.

FIG. 3A is a schematic diagram of a portable system 301 according to some embodiments of the invention. In some embodiments, portable system 301 includes a laser system 400 packaged in a belt-mounted enclosure 311, a delivery fiber 331, communication/control link 341 and a handpiece 351. In some embodiments, user 89 uses one or more controls on handpiece 351 to generate control signals transmitted on communication/control link 341 (in some embodiments, this communication link is electronic such as a USB cable or other serial communication link; in other embodiments, communication/control link 341 is a non-metallic fiber optic communication link particularly useful in environments hostile to metal components such as MRI machines or the like). The signals sent on communication/control link 341 control operation of laser system 400, for example setting up one or more of the modes of operation (CW, quasi-CW, random pulsed, steady pulsed, coagulation, or other modes). In some embodiments, laser system 400 is battery operated using an internal self-contained rechargeable and/or replaceable battery 321 that allows operation of system 301 for 30 minutes or more between battery recharging or replacement. Operation and structure described for handpiece 305 of FIG. 3E can be used for handpiece 351.

FIG. 3B is a schematic diagram of a portable system 302 according to some embodiments of the invention. In some embodiments, portable system 302 includes a laser system 400 packaged in a forearm-mounted enclosure 312, a delivery fiber 332, a communication/control link 347 and a handpiece 352. In some embodiments, user 89 uses one or more controls on handpiece 352 to generate control signals transmitted on communication/control link 347 (in some embodiments, this communication link is electronic such as a USB cable or other serial communication link; in other embodiments, communication/control link 347 is a non-metallic fiber optic communication link particularly useful in environments hostile to metal components such as MRI machines or the like). The signals sent on communication/control link 347 control operation of laser system 400, for example setting up one or more of the modes of operation (CW, quasi-CW, random pulsed, steady pulsed, coagulation, or other modes). In some embodiments, laser system 401 is battery operated using an internal self-contained rechargeable and/or replaceable battery 322 that allows operation of system 302 for 30 minutes or more between battery recharging or replacement. Operation and structure described for handpiece 305 of FIG. 3E can be used for handpiece 352.

Figure 3C:
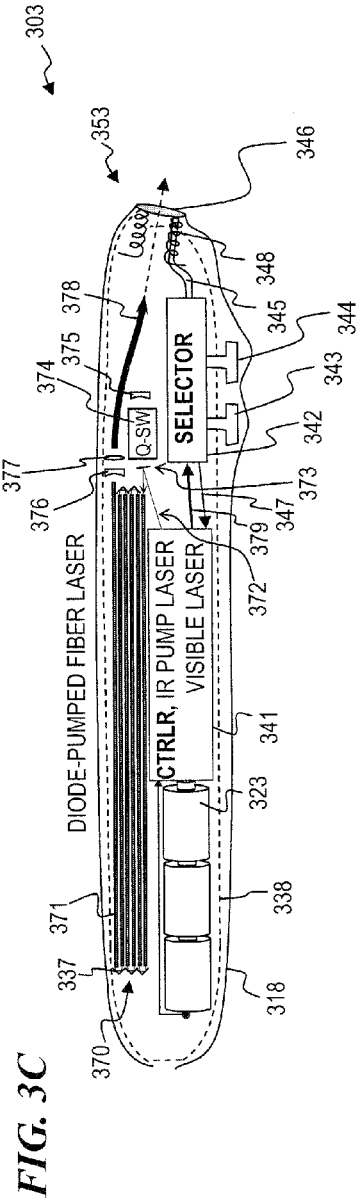
FIG. 3C is a schematic diagram, partially in cross section, of a portable system 303 according to some embodiments of the invention.

FIG. 3C is a schematic diagram, partially in cross section, of a portable system instrument 303 according to some embodiments of the invention. In some embodiments, portable system instrument 303 includes a self-contained handpiece 353. In some embodiments, handpiece 353 includes an inner housing 338 that is (when used in an operating environment) surrounded by a replaceable sterile outer sheath 318. Within housing 338 are the power supply (e.g. one or more batteries 323) that can be recharged and/or replaced. Batteries 323 provide power to controller-and-laser unit 341. In some embodiments, controller-and-laser unit 341 include one or more IR-wavelength pump lasers that output IR pump laser beam 372 and one or more visible-wavelength lasers that output visible pointer laser light 379. Controller 341 further controls the operation of Q-switch 374, which determines whether laser 370 operates in CW mode, quasi-CW mode, long-pulse thermal ablation mode, short-pulse non-thermal ablation mode, coagulation mode or other optional operation modes. Laser 370, in some embodiments, includes a plurality of Tm-doped fiber rods 371 (in some embodiments, these are photonic crystal rods (PCRs) such as described in U.S. Pat. No. 7,260,299, which is assigned to the assignee of the present invention, and which is incorporated herein by reference, however in some embodiments of the present invention the PCRs are Tm-doped; in other embodiments, these could be Tm-doped fiber sections 371) that are optically coupled to one another using double-mirror reflectors 337 between adjacent pairs of laser PCRs 371. In some embodiments, laser 370 further includes a dichroic mirror 373 that reflects pump light 372 into the end of one of the laser rods while transmitting signal light from the laser rod to the Q-switch 374, and high reflectivity mirror 375 that form one end of the non-ring laser, and partial reflecting output mirror 376 at the opposite end of the non-ring laser 370. The output beam of laser 370 is focused by lens 377 into the end of delivery fiber 378 and upon exiting delivery fiber 378 is propagated to the surgery site through output optics 346 (e.g. a lens). In some embodiments, lens 346 must be pressed against the tissue being operated on, and this condition is detected by spring-force detectors 348 whose output signal is routed through selector 342 into controller 341 using communication-control link 347. In some embodiments, handpiece 353 includes one or more function selection buttons 343 and one or more activation buttons 344, wherein the function selection button 343 causes a unique visible light indication 379 delivered through optical path 345 (e.g., an acrylic rod or optical fiber) for each of the various functions of handpiece 353. For example, cutting mode may be indicated by a red laser-diode output, coagulation mode may be indicated by green laser-diode output, fractional photolysis mode may be indicated by blue laser-diode output, and the like for other modes. Alternatively, the visible light may be pulsed at different pulse patterns to indicate which of the various function has been activated. Optionally, one of the modes of operation selectable by button 343 or by extended time non-use of the instrument 303 would be turning the instrument 303 off. In some embodiments, an audible audio signal is output to indicate the selected mode (some embodiments use a synthesized voice output telling the user which mode has been selected or is operating; other embodiments use musical tones or other audio indicators). In some embodiments, once a mode is selected and its identity provided by the visible and/or audible indication, the user activates button 344 to engage or enable the selected function (e.g., a cutting mode upon being selected starts a red visible light indicator pointing to the location that will be cut, and upon activation of button 344 the ultra-short cutting pulses generated by the modulation of Q-switch 374 under the control of controller 341 would begin; upon release of button 344 the cutting operation would stop but the red visible indicator would continue to show that the instrument 303 was in cutting mode; after a period of inactivity the instrument 303 would turn off and the red visible indicator would cease).

Figure 3D:
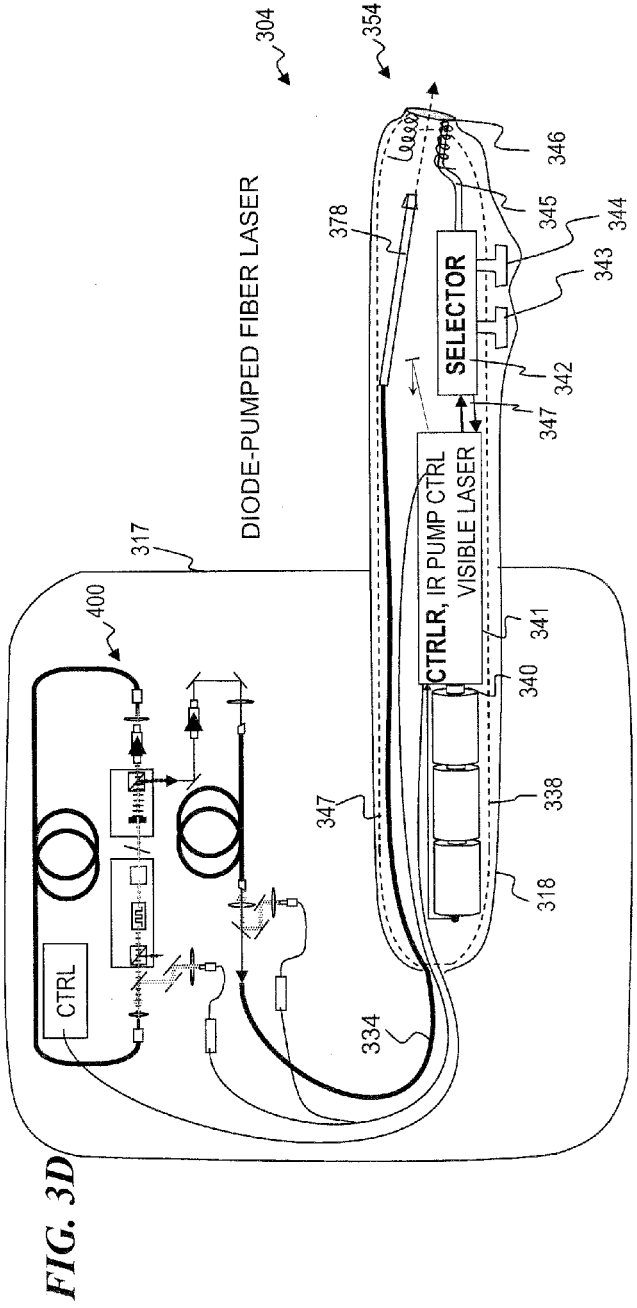
FIG. 3D is a schematic diagram, partially in cross section, of a portable system 304 according to some embodiments of the invention.

FIG. 3D is a schematic diagram, partially in cross section, of a portable system 304 according to some embodiments of the invention. In some embodiments, portable system 304 includes a multiple-mode laser system 400 that is controlled by controller 341 in a manner such as described above. In some embodiments, an inner housing 338 is covered by a replaceable outer sheath 318. In some embodiments, a flexible substrate 317 is used to mount the components of fiber laser MMLS 400 and substrate 317 is then wrapped around the housing 338 and later covered by sheath 318. Other aspects and reference numerals relative to FIG. 3D are as described in FIG. 3C, and FIG. 4 relative to MMLS 400.

FIG. 3E is a schematic diagram, partially in cross section, of a portable system 305 according to some embodiments of the invention. In some embodiments, portable system 305 includes a multiple-mode laser system 400 that is controlled by controller 341 in a manner such as described above. In some embodiments, an inner housing 338 is covered by a replaceable outer sheath 318. In some embodiments, an external enclosure 317 is used to mount the components of fiber laser MMLS 400. Other aspects and reference numerals relative to FIG. 3E are as described in FIG. 3C, and FIG. 4 relative to MMLS 400. System 305, however, has an enhanced optical delivery head 353 that includes a transparent body, a magnifying viewport 359 and a tissue facing application face 399. In some embodiments, a plurality of laser beam delivery ends are provided for example, including a cutting delivery end 333 used to deliver tightly focused tissue ablating pulses, a coagulation delivery end 334 configured to generate a long and moderately narrow output beam spread over the surface of the patient's skin and extending from one end 336 to an opposite end 337 (in some embodiments, for example, the distance between 336 and 337 is approximately 1 cm and the spot is approximately 1 mm wide). In some embodiments, a visible pattern generating delivery end 335 is used to project a pattern that indicates to the surgeon 88 exactly where the cutting and/or coagulation energy will be delivered. For example, in some embodiments, indicator delivery end 335 generates a pointed icon 330 having a sharp tip 339 as shown in FIG. 3G.

In any of the embodiments herein referring to a MMLS 400 any of the multiple mode laser systems 401, 501, 601, 701 or 801 can be used for the generic MMLS 400. MMLS 400 can also be embodied by any other suitable laser system of the appropriate power, pulse control, and other characteristics as described herein.

FIG. 3F is a schematic diagram, of an end view of delivery optic face 353 of a portable system 305 according to some embodiments of the invention. The pattern shown indicates the visible indication of the area of tissue that would be coagulated by a coagulation mode of the system and would coagulate from end 336 to end 337 at the bottom.

FIG. 3G is a schematic diagram, of an end view of delivery optic face 353, of a portable system 305 according to some embodiments of the invention. In some embodiments, an icon 330 is projected on the patient's skin through face 399 of optics head 353. Icon 330, in some embodiments, is large enough for quick visual acquisition of the mode of operation and the fact that cutting would occur at the sharp tip 339 of icon 330. That is, icon 330 does not represent the cutting beam that is emitted from delivery head 330, but rather is a visual indication, projected from delivery head 335, showing where the cutting beam will be aimed when it is activated.

FIG. 3H is a schematic perspective view of a portable system 308 according to some embodiments of the invention. In some embodiments, system 308 is a small form factor portable ruggedized laptop unit with housing 383, a power button 382, MMLS 400 including a controller and power supply (e.g., one or more batteries) and contains a flip-top screen 384 with touch-screen controls for providing user input signals to the controller. In some embodiments, output signal 381 is delivered to a handpiece 305 such as described in FIG. 3E. In some embodiments, control signals from handpiece 305 are passed back to system 308 using communication links within the same jacket as delivery fiber 381.

FIG. 3i is a schematic perspective view of a portable system 309 according to some embodiments of the invention. In some embodiments, system 309 is a small form factor portable ruggedized laptop unit with a housing 383, a power button 382, MMLS 400 including a controller and power supply (e.g., one or more batteries) and contains a flip-top screen 384 with touch-screen controls for providing user input signals to the controller. In some embodiments, output signal 381 is delivered to a handpiece 305 such as described in FIG. 3E. In some embodiments, control signals from handpiece 305 are passed back to system 308 using communication links within the same jacket as delivery fiber 381.

Figure 4:
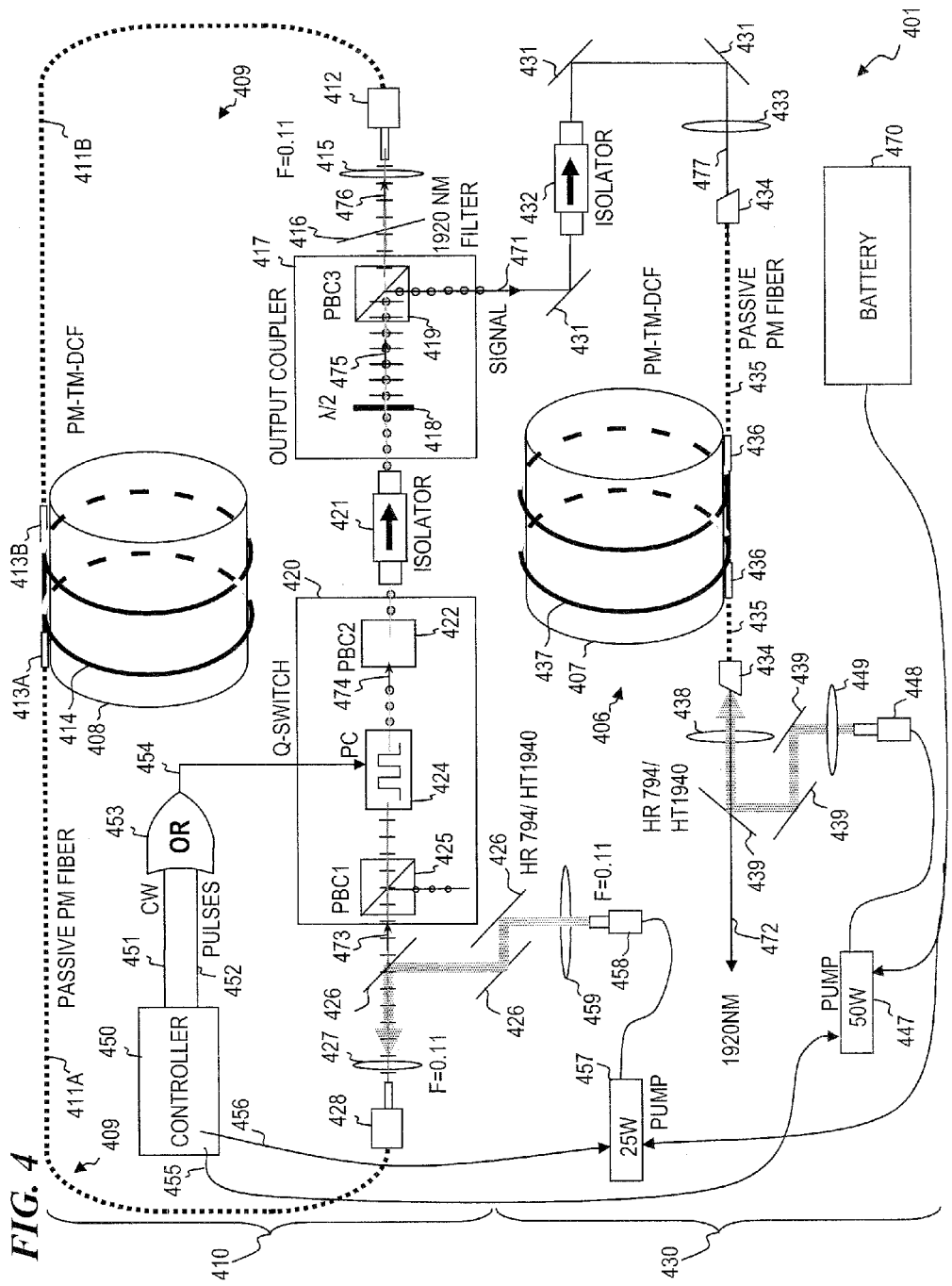
FIG. 4 is a schematic block diagram of a multiple-mode laser system 401 according to some embodiments of the invention.

FIG. 4 is a schematic block diagram of a multiple-mode laser system (MMLS) 401 according to some embodiments of the invention. In some embodiments, MMLS 401 includes a single laser capable of operating in one or more of a plurality of modes (e.g., continuous wave (CW) or quasi-CW, long pulse, short pulse, or an overlapped-in-time combination of two or more of these modes). In some embodiments, a master-oscillator power-amplifier (MOPA) configuration is used such as shown in FIG. 4, wherein MMLS 401 includes a master-oscillator portion 410 and a power-amplifier portion 430. In some embodiments, a ring-oscillator configuration (a ring laser that generates a seed signal 471 later amplified by the power amplifier 430) is used for master-oscillator portion 410, wherein pump light is launched in a counter-propagating direction (e.g., clockwise direction in FIG. 4) through a lens 427 into a fiber endcap and/or ferrule 428. In some embodiments, a fiber portion 409 includes endcap 428, passive polarization-maintaining (PM) fiber 411A, splice 413A, PM gain fiber 414, another splice 413B, another passive PM fiber 411B, and another endcap 412. In some embodiments, gain fiber 414 is a polarization-maintaining thulium-doped (Tm-doped) double-clad (PM-TM-DCF) fiber having a large mode area (LMA). For example, some embodiments use a fiber (e.g., in some embodiments, the length of gain fiber 414 is in the range of 1-5 meters long) having a core diameter of about 10 microns to about 25 microns and an outer diameter of between about 250 microns and about 400 microns (e.g., fibers such as these are available or can be ordered from companies such as Nufern, 7 Airport Park Road, East Granby, Conn. 06026, Coractive, 2700 Jean-Perrin, Suite 121, Quebec (Qc), Canada, G2C 1S9, or OFS, 2000 Northeast Expressway, Norcross, Ga., 30071). In some embodiments, the first section 411A of the fiber portion 409 of the ring master oscillator 410 is a passive (e.g., a substantially non-doped fiber) polarization-maintaining (PM) fiber (rather than an active gain fiber) in order to minimize the heating of this portion of the fiber from the pump and signal light. In some embodiments, the length of passive fiber is calculated or empirically determined and adjusted to be of a length suitable for stable lasing at the desired signal wavelength. In some embodiments, a section of gain fiber 414 is spliced to the passive PM fiber 411A and 411B at splices 413A and 413B, in order that the gain fiber 414 can be more fully wrapped around a cooling mandrel 408 (in some embodiments, mandrel 408 is actively cooled, for example by pumping water through tubing attached to heat conducting metal of the mandrel 408 while in other embodiments, mandrel 408 provides a passively cooled heat sink function) to counteract the heating effects of the pump and signal light. This configuration of passive-active-passive fiber allows substantially all the gain fiber to be in intimate contact with the cooling mandrel 408. The right-hand splice 413B connects the PM gain fiber 414 to a second passive PM fiber 411B in the upper-right portion of FIG. 4, which is then connected into a fiber endcap and/or ferrule 412, such that feedback signal light 476 "left over" from output coupler 417 is wavelength-bandpass filtered through filter 416 (in some embodiments, this filter is tuned to transmit light having a wavelength of 1945 nm, one of the wavelengths facilitated by the Tm-doping in the gain fiber 414), focused by lens 415, and launched (relative to the orientation in FIG. 4) into the right-hand endcap 412 of fiber 411B in a counter-clockwise (CCW) direction into the fiber portion 409. In some embodiments, the numeric aperture (NA) of fiber section 409 is in the range of approximately 0.08 to 0.12 (e.g., F=0.11 in some embodiments).

In some embodiments, signal light traveling in the counter-clockwise direction in master-oscillator fiber 409 exits the left-end of passive fiber 409 through fiber endcap and/or ferrule 428 and is collimated by collimating lens 427, passes through dichroic mirror 426 (in some embodiments, each of these dichroic mirrors 426 (and each of the dichroic mirrors 439 of the power amplifier stage 430) are highly reflective to light having a wavelength of 794 nm (or whichever wavelength is used for the pump light) and highly transmissive to light having a wavelength of approximately 1940-1945 nm (or whichever wavelength is used for the signal light) and enters Q-switch 420 (from left-to-right in FIG. 4). In some embodiments, Q-switch 420 is controlled by controller 450 and OR gate 453 that send electrical signal 454 to Pockels cell 424 to cause Pockels cell 424 to modulate (adjust) the polarization of the signal light in order to control the output of the signal light from the right end of Q-switch 420. In some embodiments, controller 450 and OR gate 453 provide the means for selecting various operation modes of the MMLS 401 (e.g., a CW mode or quasi-CW mode achieved by outputting a "TRUE" signal on the CW line 451 to the OR gate 453, short-pulsed mode achieved by outputting a "FALSE"

signal on the CW input to OR gate 453 and a series of short pulses to the pulses line 452, long-pulsed mode achieved by outputting a "FALSE" signal on the CW input to OR gate 453 and a series of long pulses to the pulses line 452, or the like) by providing the input electrical signals, 451 and 452 respectably, to logical OR gate 453 to control Pockels cell 424 via electrical signal 454. In some embodiments, the mode of MOPA 401 is also controlled by control signal 456 between controller 450 and master-oscillator pump laser 457 and/or control signal 455 between controller 450 and power-amplifier pump laser 447. For example, when in pulsed mode there is no need to pump master-oscillator 410 or power-amplifier 430 for a longer precharge than the typical pulse-to-pulse spacing between pulses for the mode desired (i.e., if operating at a 10000 Hz pulse repetition rate (PRR) the pulse-to-pulse spacing is 100 microseconds; thus the master oscillator pump 457 and the power amplifier pump 447 would not be activated until 100 microseconds before the first pulse that is desired—that is a time indistinguishable from "instant on" relative to the activation by the user pressing the button to activate this short pulse mode. In fact, if a larger pre-charge time were allowed when the pump lasers are on but lasing is not allowed than the first lasing pulse would have an inordinately large power and energy content due to the longer time period to accumulate pump energy. Further, pumping into the gain fiber 414 when no output is desired causes unnecessary heating of the gain fiber 414 and the mandrel 408 (also for gain fiber 437 and mandrel 407 of the power amplifier).

In some embodiments, when the Pockels cell 424 is not activated (i.e., when the Q-switch 420 is turned OFF in order to prevent lasing) by the electrical signal 454 (i.e., when the Pockels cell 424 does not rotate the polarization of signal light 473), the signal light 474 (which was polarized to a plane in the plane of the sheet of the FIG. 4 drawing paper by polarizing beam cube (PBC1) 425, as indicated by the vertical cross markings on the signal light 473 between endcap 428 and Pockels cell 424) will be substantially blocked by polarizing beam cube (PBC2) 422 such that substantially no signal light is output through the right end of Q-switch 420 and the master-oscillator laser ring 410 will not lase when the Q-switch is in this OFF state. On the other hand, when the Pockels cell 424 is activated (i.e., when the Q-switch 420 is turned ON in order to facilitate lasing) by the electrical signal 454 (i.e., when the Pockels cell 424 rotates the polarization of signal light 473 by substantially 90 degrees such that signal light 474, as indicated by small circles indicating polarization perpendicular to the drawing sheet of FIG. 4), the signal light 474 (which was polarized to a plane in the plane of the sheet of the FIG. 4 drawing paper by polarizing beam cube (PBC1) 425, as indicated by the vertical cross markings on the signal light 473 between PBC1 425 and Pockels cell 424 and the polarization perpendicular to the drawing sheet as indicated by the small circles) will be substantially passed by polarizing beam cube (PBC2) 422 such that substantially all of the signal light is output through the right end of Q-switch 420 and the master-oscillator laser ring 410 will lase when the Q-switch is in this ON state.

In some embodiments, when the master oscillator ring laser is lasing, electrical signal 454 (in some embodiments, this signal is on the order of a kilovolt or more when active) activates Pockels cell 424 to rotate the polarization of the signal light by substantially 90 degrees (as indicated by the circles on the signal light between Pockels cell (PC) 424. The $\lambda/2$ waveplate 418 is used to rotate the polarization of signal light 474 by a variable amount to generate signal light 475 having a polarization direction partially in the plane of the drawing sheet and partially in the direction perpendicular of the drawing sheet as indicated by both small-circles and vertical cross-marks on signal light 475, in order that an adjustable proportion of the signal light 475 will pass through polarizing beam cube 422 to become feedback signal 476 for the lasing operation, and the remaining signal light 471 exits the output coupler 417 as the output of master-oscillator laser ring 410 when lasing.

In some embodiments, isolator 421 allows signal light 474 to pass only in the left-to-right direction (CCW in the ring). This applies only to the signal light, since the pump light which is injected in the clockwise direction at endcap 428 is substantially absorbed by gain fiber 414 and blocked by the 1945-nm bandpass filter 416. Thus, signal light 471 that exits the Q-switch 420 passes through isolator 421 (used for obtaining unidirectional signal light propagation in the ring of master-oscillator 410) and enters output coupler 417 where the signal light passes through waveplate 418 (used for rotating the signal light polarization by an amount such that, in some embodiments, approximately about 30 percent of the signal light will be transmitted through polarizing beam cube 419 to form a feedback signal 476 for the ring laser and about 70 percent of the signal light will be reflected to form an intermediate output signal beam 471.

In some embodiments, intermediate output signal 471 is reflected by zero or more reflectors 431 and passed through optional isolator 432 (used to prevent spurious backward traveling signal from the power amplifier from disrupting operation of the master oscillator 410. The signal light is then focused by lens 433 into endcap 434 of power amplifier fiber 406. As was the case for the master oscillator fiber 409, in some embodiments, power amplifier fiber 406 includes a pair of passive PM fibers 435, one spliced to each end of active gain fiber 437 by splices 436. In some embodiments, gain fiber 437 is wound on a cooling mandrel 407. In some embodiments, the signal output from power amplifier 406 is coupled out of the left endcap 434 and collimated by lens 438 to form an output beam 472 after passing through one of the dichroic mirrors 439. In some embodiments, power amplifier pump laser 447 (in some embodiments, this is a 50 Watt semiconductor laser bar that generates pump light having a wavelength of approximately 794 nm, which is effectively absorbed by gain fiber 437 in order to amplify signal light 477 to form output signal beam 472. Also note that in some embodiments master oscillator pump 457 is a 25 Watt semiconductor laser bar that generates pump light also having a wavelength of approximately 794 nm, which is effectively absorbed by gain fiber 414 in order to amplify feedback signal light 476 to form the intermediate output signal beam 471.

In some embodiments, pump light from pump 457 is delivered through endcap 458 and collimated by lens 459 and then reflected by one or more dichroic mirrors 426 and then through focusing lens 427 into endcap 428 in a counter-propagating direction relative to the lasing signal light 473 in gain fiber 414. In some embodiments, pump light from pump 447 is delivered through endcap 448 and collimated by lens 449 and then reflected by one or more dichroic mirrors 439 and then through focusing lens 438 into endcap 434 in a counter-propagating direction relative to the signal light in gain fiber 437.

In some embodiments, a portable power supply 470 (e.g., in some embodiments, power supply 470 includes a rechargeable battery) is used to supply electrical power to pump lasers 447 and 457 under the control of controller 450.

Figure 5:
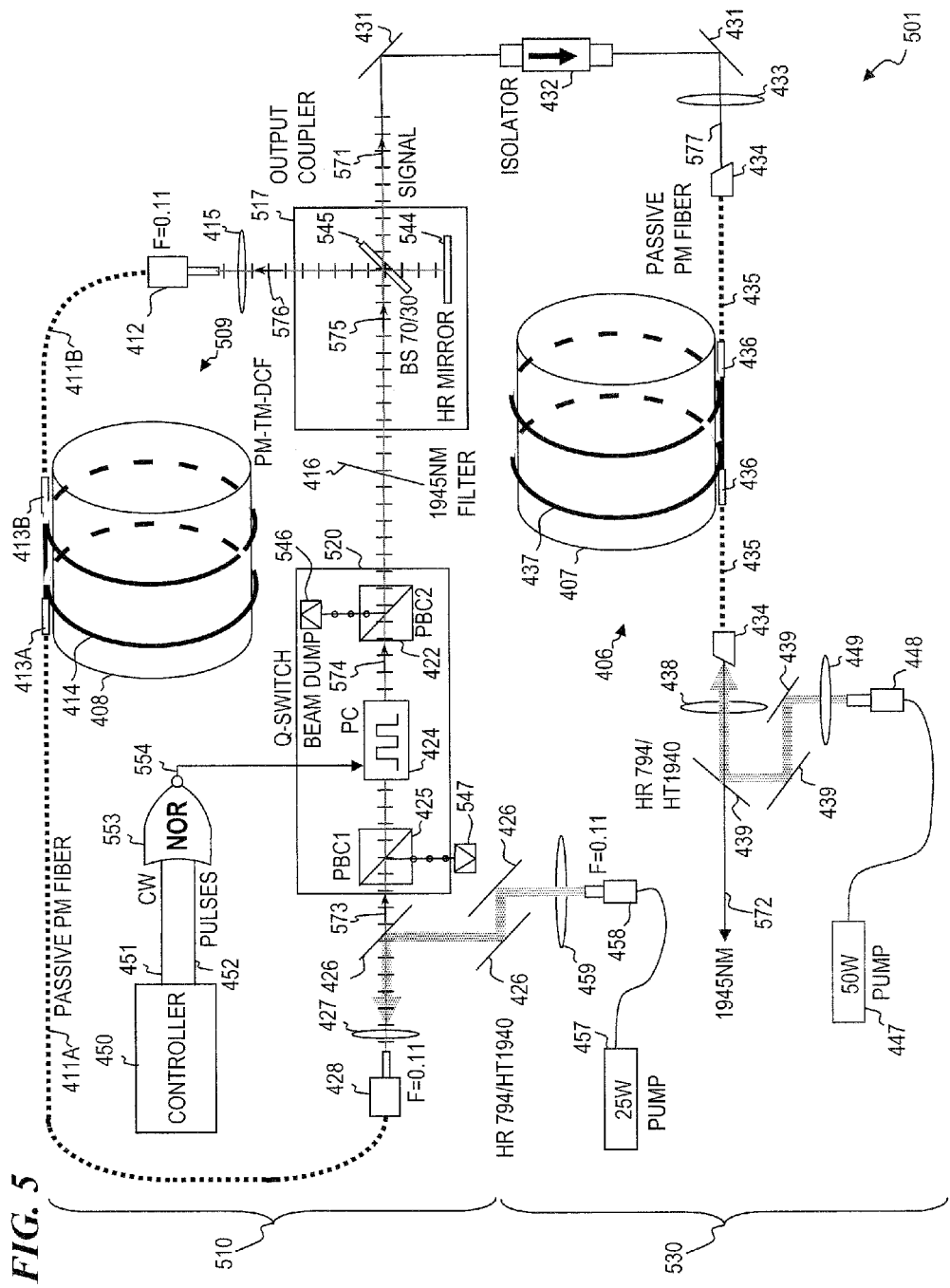
FIG. 5 is a schematic block diagram of a multiple-mode laser system 501 according to some embodiments of the invention.

FIG. 5 is a schematic block diagram of a multiple-mode laser system 501 according to some embodiments of the invention. Elements of MMLS 501 having reference numbers corresponding to similar elements in MMLS 401 of FIG. 4 provide substantially similar functions. The differences in FIG. 5, relative to FIG. 4, include replacing isolator 421 of FIG. 4 by high-reflectivity (HR) mirror 444 in FIG. 5; moving bandpass filter 416 to the high power side of output coupler 457.

Thus, MMLS 501 includes a single laser capable of operating in one or more of a plurality of modes (e.g., continuous wave (CW) or quasi-CW, long pulse, short pulse, or an overlapped-in-time combination of two or more of these modes). In some embodiments, a master-oscillator power-amplifier (MOPA) configuration is used such as shown in FIG. 5, wherein MMLS 501 includes a master-oscillator portion 510 and a power-amplifier portion 530. In some embodiments, a ring-oscillator configuration (a ring laser that generates a seed signal 571 later amplified by the power amplifier 530) is used for master-oscillator portion 510, wherein pump light is launched in a counter-propagating direction (e.g., clockwise direction in FIG. 5) through a lens 427 into a fiber endcap and/or ferrule 428. In some embodiments, a fiber portion 509 includes endcap 428, passive polarization-maintaining (PM) fiber 411A, splice 413A, PM gain fiber 414, another splice 413B, another passive PM fiber 411B, and another endcap 412. Note that in this configuration endcaps 428 and 412 are perpendicular to one another due to the different configuration of output coupler 517.

In some embodiments, gain fiber 414 is a polarization-maintaining thulium-doped (Tm-doped) double-clad (PM-TM-DCF) fiber having a large mode area (LMA). For example, some embodiments use a fiber (e.g., in some embodiments, the length of gain fiber 414 is in the range of 1-5 meters long) having a core diameter of about 10 microns to about 25 microns and an outer diameter of between about 250 microns and about 400 microns (e.g., fibers such as these are available or can be ordered from companies such as Nufern, 7 Airport Park Road, East Granby, Conn. 06026, Coractive, 2700 Jean-Perrin, Suite 121, Quebec (Qc), Canada, G2C 1S9, or OFS, 2000 Northeast Expressway, Norcross, Ga., 30071). In some embodiments, the first section 411A of the fiber portion 509 of the ring master oscillator 510 is a passive (e.g., a substantially non-doped fiber) polarization-maintaining (PM) fiber (rather than an active gain fiber) in order to minimize the heating of this portion of the fiber from the pump and signal light. In some embodiments, the length of passive fiber is calculated or empirically determined and adjusted to be of a length suitable for stable lasing at the desired signal wavelength. In some embodiments, a section of gain fiber 414 is spliced to the passive PM fiber 411A and 411B at splices 413A and 413B, in order that the gain fiber 414 can be more fully wrapped around a cooling mandrel 408 (in some embodiments, mandrel 408 is actively cooled, for example by pumping water through tubing attached to heat conducting metal of the mandrel 408 while in other embodiments, mandrel 408 provides a passively cooled heat sink function) to counteract the heating effects of the pump and signal light. This configuration of passive-active-passive fiber allows substantially all the gain fiber to be in intimate contact with the cooling mandrel 408. The right-hand splice 413B connects the PM gain fiber 414 to a second passive PM fiber 411B in the upper-right portion of FIG. 5, which is then connected into a fiber endcap and/or ferrule 412, such that feedback signal light 576 "left over" (reflected upward by beam splitter 545) from output coupler 517 is focused by lens 415, and launched (relative to the orientation in FIG. 5) into the right-hand endcap 412 of fiber 411B in a counter-clockwise (CCW) direction into the fiber portion 509. In some embodiments, the numeric aperture (NA) of fiber section 509 is in the range of approximately 0.08 to 0.12 (e.g., F=0.11 in some embodiments).

In some embodiments, signal light 573 traveling in the counter-clockwise direction in master-oscillator fiber 409 exits the left-end of passive fiber 409 through fiber endcap and/or ferrule 428 and is collimated by collimating lens 427, passes through dichroic mirror 426 (in some embodiments, each of these dichroic mirrors 426 (and each of the dichroic mirrors 439 of the power amplifier stage 430) are highly reflective to light having a wavelength of 794 nm (or whichever wavelength is used for the pump light) and highly transmissive to light having a wavelength of approximately 1940-1945 nm (or whichever wavelength is used for the signal light) and enters Q-switch 520 (from left-to-right in FIG. 5). In some embodiments, Q-switch 520 is controlled by controller 450 and NOR gate 553 that send electrical signal 454 to Pockels cell 424 to cause Pockels cell 424 to modulate (adjust) the polarization of the signal light in order to control the output of the signal light from the right end of Q-switch 520. In some embodiments, controller 450 and NOR gate 553 provide the means for selecting various operation modes of the MMLS 501 (e.g., a CW mode or quasi-CW mode achieved by outputting a "TRUE" signal on the CW line 451 to the NOR gate 553, short-pulsed mode achieved by outputting a "FALSE" signal on the CW input to NOR gate 553 and a series of short pulses to the pulses line 452, long-pulsed mode achieved by outputting a "FALSE" signal on the CW input to NOR gate 553 and a series of long pulses to the pulses line 452, or the like) by providing the input electrical signals, 451 and 452 respectably, to logical NOR gate 553 to control Pockels cell 424 via electrical signal 554 (note that the polarity of electrical signal 554 is the logical inverse of the polarity if electrical signal 454 of FIG. 4). In some embodiments, the mode of MOPA 501 is also controlled by controller 450 controlling master-oscillator pump laser 457 and/or power-amplifier pump laser 447. For example, when in pulsed mode there is no need to pump master-oscillator 510 or power-amplifier 530 for a longer precharge of their respective fibers with pump light for a time longer than the typical pulse-to-pulse spacing between pulses for the mode desired (i.e., if operating at a 10000 Hz pulse repetition rate (PRR) the pulse-to-pulse spacing is 100 microseconds; thus the master oscillator pump 457 and the power amplifier pump 447 would not be activated until 100 microseconds before the first pulse that is desired—that is a time indistinguishable from "instant on" relative to the activation by the user pressing the button to activate this short pulse mode. In fact, if a larger pre-charge time were allowed when the pump lasers are on but lasing is not allowed than the first lasing pulse would have an inordinately large power and energy content due to the longer time period to accumulate pump energy. Further, pumping into the gain fiber 414 when no output is desired causes unnecessary heating of the gain fiber 414 and the mandrel 408 (also for gain fiber 437 and mandrel 407 of the power amplifier).

In some embodiments, when the Pockels cell 424 is activated (i.e., when the Q-switch 520 is turned OFF in order to prevent lasing) by the electrical signal 554 (i.e., when the Pockels cell 424 does rotate the polarization of signal light 573 by substantially 90 degrees), the signal light 574 (which was polarized to a plane in the plane of the sheet of the FIG. 5 drawing paper by polarizing beam cube (PBC1) 425, as indicated by the vertical cross markings on the signal light 573 between endcap 428 and Pockels cell 424) will be substantially blocked by polarizing beam cube (PBC2) 422 such that substantially no signal light is output through the right end of Q-switch 520 and the master-oscillator laser ring 510 will not lase when the Q-switch is in this OFF state. Note that for this configuration PBC1 425 and PBC2 422 are oriented in the same direction such that when the Pockels cell 424 does not rote the polarization of the beam, ring laser 510 will lase, which is the opposite relative to FIG. 4. On the other hand, when the Pockels cell 424 is not activated (i.e., when the Q-switch 520 is turned ON in order to facilitate lasing) by the electrical signal 554 (i.e., when the Pockels cell 424 does not rotate the polarization of signal light 473 such that signal light 574, as indicated by the vertical cross-marks indicating polarization parallel to the drawing sheet of FIG. 5), the signal light 574 (which was polarized to a plane in the plane of the sheet of the FIG. 5 drawing paper by polarizing beam cube (PBC1) 425, as indicated by the vertical cross markings on the signal light 573 between PBC1 425 and Pockels cell 424 and the polarization parallel to the drawing sheet as indicated by the vertical cross-marks) will be substantially passed by polarizing beam cube (PBC2) 422 such that substantially all of the signal light is output through the right end of Q-switch 520 and the master-oscillator laser ring 510 will lase when the Q-switch is in this ON state.

In some embodiments, when the master oscillator ring laser 510 is lasing, electrical signal 554 (in some embodiments, this signal is on the order of a kilovolt or more when the ring is not lasing, but no voltage is applied when lasing) activates Pockels cell 424 to not rotate the polarization of the signal light (as indicated by the vertical cross-marks on the signal light between Pockels cell (PC) 424. The λ/2 waveplate 418 of FIG. 4 (which was used to rotate the polarization of signal light 474 by a variable amount) is omitted in this configuration and instead replaced by non-polarizing beam splitter 545, in order that a predetermined proportion of the signal light 575 will reflect from beam splitter 545 to become feedback signal 576 for the lasing operation, and the remaining signal light 571 passes through the beam splitter 545 and out the right side of output coupler 517 as the output of master-oscillator laser ring 510 when lasing.

In some embodiments, beam splitter 545 and HR mirror 544 encourage signal light 574 to pass only in the CCW direction in the ring. This applies only to the signal light, since the pump light which is injected in the clockwise direction at endcap 428 is substantially absorbed by gain fiber 414 and blocked by the 1945-nm bandpass filter 416.

In some embodiments, intermediate output signal 571 is reflected by zero or more reflectors 431 and passed through optional isolator 432 (used to prevent spurious backward traveling signal from the power amplifier from disrupting operation of the master oscillator 510. The signal light is then focused by lens 433 into endcap 434 of power amplifier fiber 506. As was the case for the master oscillator fiber 509, in some embodiments, power amplifier fiber 506 includes a pair of passive PM fibers 435, one spliced to each end of active gain fiber 437 by splices 436. In some embodiments, gain fiber 437 is wound on a cooling mandrel 407. In some embodiments, the signal output from power amplifier 506 is coupled out of the left endcap 434 and collimated by lens 438 to form an output beam 572 after passing through one of the dichroic mirrors 439. In some embodiments, power amplifier pump laser 447 (in some embodiments, this is a 50 Watt semiconductor laser bar that generates pump light having a wavelength of approximately 794 nm, which is effectively absorbed by gain fiber 437 in order to amplify signal light 577 to form output signal beam 572. Also note that in some embodiments master oscillator pump 457 is a 25 Watt semiconductor laser bar that generates pump light also having a wavelength of approximately 794 nm, which is effectively absorbed by gain fiber 414 in order to amplify feedback signal light 576 to form the intermediate output signal beam 571.

In some embodiments, pump light from pump 457 is delivered through endcap 458 and collimated by lens 459 and then reflected by one or more dichroic mirrors 426 and then through focusing lens 427 into endcap 428 in a counter-propagating direction relative to the lasing signal light 573 in gain fiber 414. In some embodiments, pump light from pump 447 is delivered through endcap 448 and collimated by lens 449 and then reflected by one or more dichroic mirrors 439 and then through focusing lens 438 into endcap 434 in a counter-propagating direction relative to the signal light 577 in gain fiber 437.

In some embodiments, a portable power supply 470 (e.g., in some embodiments, power supply 470 includes a rechargeable battery) is used to supply electrical power to pump lasers 447 and 457 under the control of controller 450.

Figure 6:
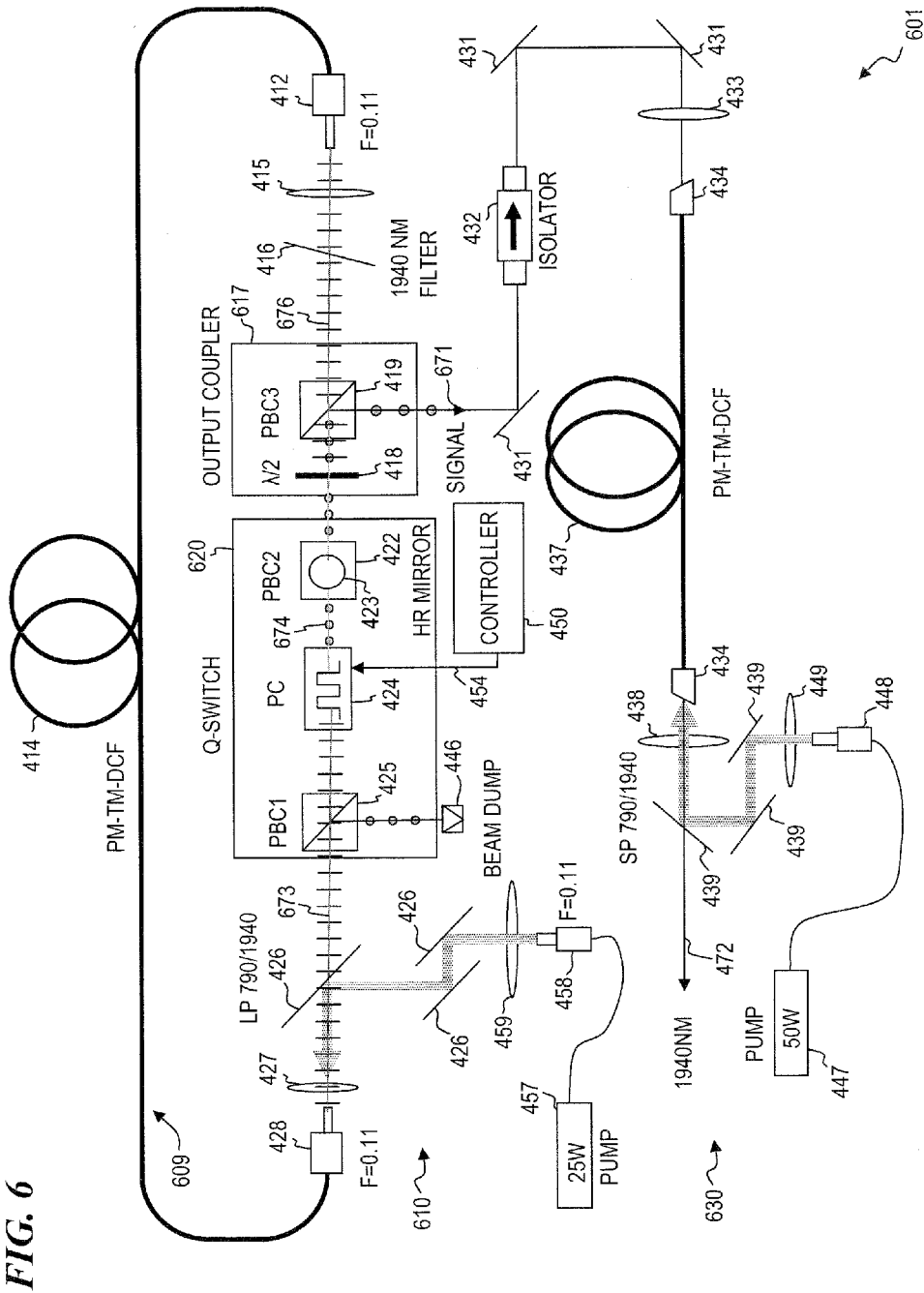
FIG. 6 is a schematic block diagram of a multiple-mode laser system 601 according to some embodiments of the invention.

FIG. 6 is a schematic block diagram of a multiple-mode laser system 601 according to some embodiments of the invention. Elements of MMLS 601 having reference numbers corresponding to similar elements in MMLS 401 of FIG. 4 provide substantially similar functions. The differences in FIG. 6, relative to FIG. 4, include replacing isolator 421 of FIG. 4 by high-reflectivity (HR) mirror 423 in FIG. 6. In other aspects, MMLS 601 operates in the same manner as MMLS 401.

Thus, MMLS 601 includes a single laser capable of operating in one or more of a plurality of modes (e.g., continuous wave (CW) or quasi-CW, long pulse, short pulse, or an overlapped-in-time combination of two or more of these modes). In some embodiments, a master-oscillator power-amplifier (MOPA) configuration is used such as shown in FIG. 6, wherein MMLS 601 includes a master-oscillator portion 610 and a power-amplifier portion 630. In some embodiments, a ring-oscillator configuration (a ring laser that generates a seed signal 671 later amplified by the power amplifier 630) is used for master-oscillator portion 610, wherein pump light is launched in a counter-propagating direction (e.g., clockwise direction in FIG. 6) through a lens 427 into a fiber endcap and/or ferrule 428. In some embodiments, a fiber portion 609 includes endcap 428, PM gain fiber 414, and another endcap 412.

In some embodiments, gain fiber 414 is a polarization-maintaining thulium-doped (Tm-doped) double-clad (PM-TM-DCF) fiber having a large mode area (LMA). For example, some embodiments use a fiber (e.g., in some embodiments, the length of gain fiber 414 is in the range of 1-5 meters long) having a core diameter of about 10 microns to about 25 microns and an outer diameter of between about 250 microns and about 400 microns (e.g., fibers such as these are available or can be ordered from companies such as Nufern, 7 Airport Park Road, East Granby, Conn. 06026, Coractive, 2700 Jean-Perrin, Suite 121, Quebec (Qc), Canada, G2C 1S9, or OFS, 2000 Northeast Expressway, Norcross, Ga., 30071). In some embodiments, the gain fiber 414 is fully wrapped around a cooling mandrel (such as mandrel 408 shown in FIG. 4) to counteract the heating effects of the pump and signal light. In some embodiments, a fiber endcap and/or ferrule 412, receives feedback signal light 676 "left over" (transmitted by polarizing beam cube 419) from output coupler 617 is focused by lens 415, and launched (relative to the orientation in FIG. 6) into the right-hand endcap 412 in a counter-clockwise (CCW) direction into the fiber portion 609. In some embodiments, the numeric aperture (NA) of fiber section 609 is in the range of approximately 0.08 to 0.12 (e.g., F=0.11 in some embodiments).

In some embodiments, signal light 673 traveling in the counter-clockwise direction in master-oscillator fiber 609 exits the left-end of passive fiber 609 through fiber endcap and/or ferrule 428 and is collimated by collimating lens 427, passes through dichroic mirror 426 (in some embodiments, each of these dichroic mirrors 426 (and each of the dichroic mirrors 439 of the power amplifier stage 430) are highly reflective to light having a wavelength of 794 nm (or whichever wavelength is used for the pump light) and highly transmissive to light having a wavelength of approximately 1940-1945 nm (or whichever wavelength is used for the signal light) and enters Q-switch 620 (from left-to-right in FIG. 5). In some embodiments, Q-switch 620 is controlled by controller 450 that send electrical signal 454 to Pockels cell 424 to cause Pockels cell 424 to modulate (adjust) the polarization of the signal light in order to control the output of the signal light from the right end of Q-switch 620. In some embodiments, controller 450 provides the means for selecting various operation modes of the MMLS 601 (e.g., a CW mode or quasi-CW mode achieved by outputting a constant signal on the control line 454, short-pulsed mode achieved by outputting a series of short pulses on the control line 454, long-pulsed mode achieved by outputting a series of long pulses to the on the control line 454, or the like) to control Pockels cell 424. In some embodiments, the mode of MOPA 601 is also controlled by controller 450 controlling master-oscillator pump laser 457 and/or power-amplifier pump laser 447. For example, when in pulsed mode there is no need to pump master-oscillator 610 or power-amplifier 630 for a longer precharge of their respective fibers with pump light for a time longer than the typical pulse-to-pulse spacing between pulses for the mode desired (i.e., if operating at a 10000 Hz pulse repetition rate (PRR) the pulse-to-pulse spacing is 100 microseconds; thus the master oscillator pump 457 and the power amplifier pump 447 would not be activated until 100 microseconds before the first pulse that is desired—that is a time indistinguishable from "instant on" relative to the activation by the user pressing the button to activate this short pulse mode. In fact, if a larger pre-charge time were allowed when the pump lasers are on but lasing is not allowed than the first lasing pulse would have an inordinately large power and energy content due to the longer time period to accumulate pump energy. Further, pumping into the gain fiber 414 when no output is desired causes unnecessary heating of the gain fiber 414 (also for gain fiber 437 of the power amplifier).

In some embodiments, when the Pockels cell 424 is not activated (i.e., when the Q-switch 620 is turned OFF in order to prevent lasing) by the electrical signal 454 (i.e., when the Pockels cell 424 does not rotate the polarization of signal light 473), the signal light 474 (which was polarized to a plane in the plane of the sheet of the FIG. 6 drawing paper by polarizing beam cube (PBC1) 425, as indicated by the vertical cross markings on the signal light 473 between endcap 428 and Pockels cell 424) will be substantially blocked by polarizing beam cube (PBC2) 422 such that substantially no signal light is output through the right end of Q-switch 620 and the master-oscillator laser ring 610 will not lase when the Q-switch is in this OFF state. On the other hand, when the Pockels cell 424 is activated (i.e., when the Q-switch 620 is turned ON in order to facilitate lasing) by the electrical signal 454 (i.e., when the Pockels cell 424 rotates the polarization of signal light 473 by substantially 90 degrees such that signal light 674, as indicated by small circles indicating polarization perpendicular to the drawing sheet of FIG. 4), the signal light 674 (which was polarized to a plane in the plane of the sheet of the FIG. 6 drawing paper by polarizing beam cube (PBC1) 425, as indicated by the vertical cross markings on the signal light 473 between PBC1 425 and Pockels cell 424 and the polarization perpendicular to the drawing sheet as indicated by the small circles) will be substantially passed by polarizing beam cube (PBC2) 422 such that substantially all of the signal light is output through the right end of Q-switch 620 and the master-oscillator laser ring 410 will lase when the Q-switch is in this ON state.

In some embodiments, PBC2 422 and HR mirror 423 (located above (toward the viewer) and facing down towards PBC2 422) encourage signal light 674 to pass only in the CCW direction in the ring. This applies only to the signal light, since the pump light which is injected in the clockwise direction at endcap 428 is substantially absorbed by gain fiber 414 and blocked by the 1945-nm bandpass filter 416.

In some embodiments, intermediate output signal 671 is reflected by zero or more reflectors 431 and passed through optional isolator 432 (used to prevent spurious backward traveling signal from the power amplifier from disrupting operation of the master oscillator 610. The signal light is then focused by lens 433 into endcap 434 of power amplifier fiber 606. In some embodiments, gain fiber 606 is wound on a cooling mandrel. In some embodiments, the signal output from power amplifier fiber 606 is coupled out of the left endcap 434 and collimated by lens 438 to form an output beam 672 after passing through one of the dichroic mirrors 439. In some embodiments, power amplifier pump laser 447 (in some embodiments, this is a 50 Watt semiconductor laser bar that generates pump light having a wavelength of approximately 794 nm, which is effectively absorbed by gain fiber 437 in order to amplify signal light 577 to form output signal beam 572. Also note that in some embodiments master oscillator pump 457 is a 25 Watt semiconductor laser bar that generates pump light also having a wavelength of approximately 794 nm, which is effectively absorbed by gain fiber 414 in order to amplify feedback signal light 676 to form the intermediate output signal beam 671.

Figure 7:
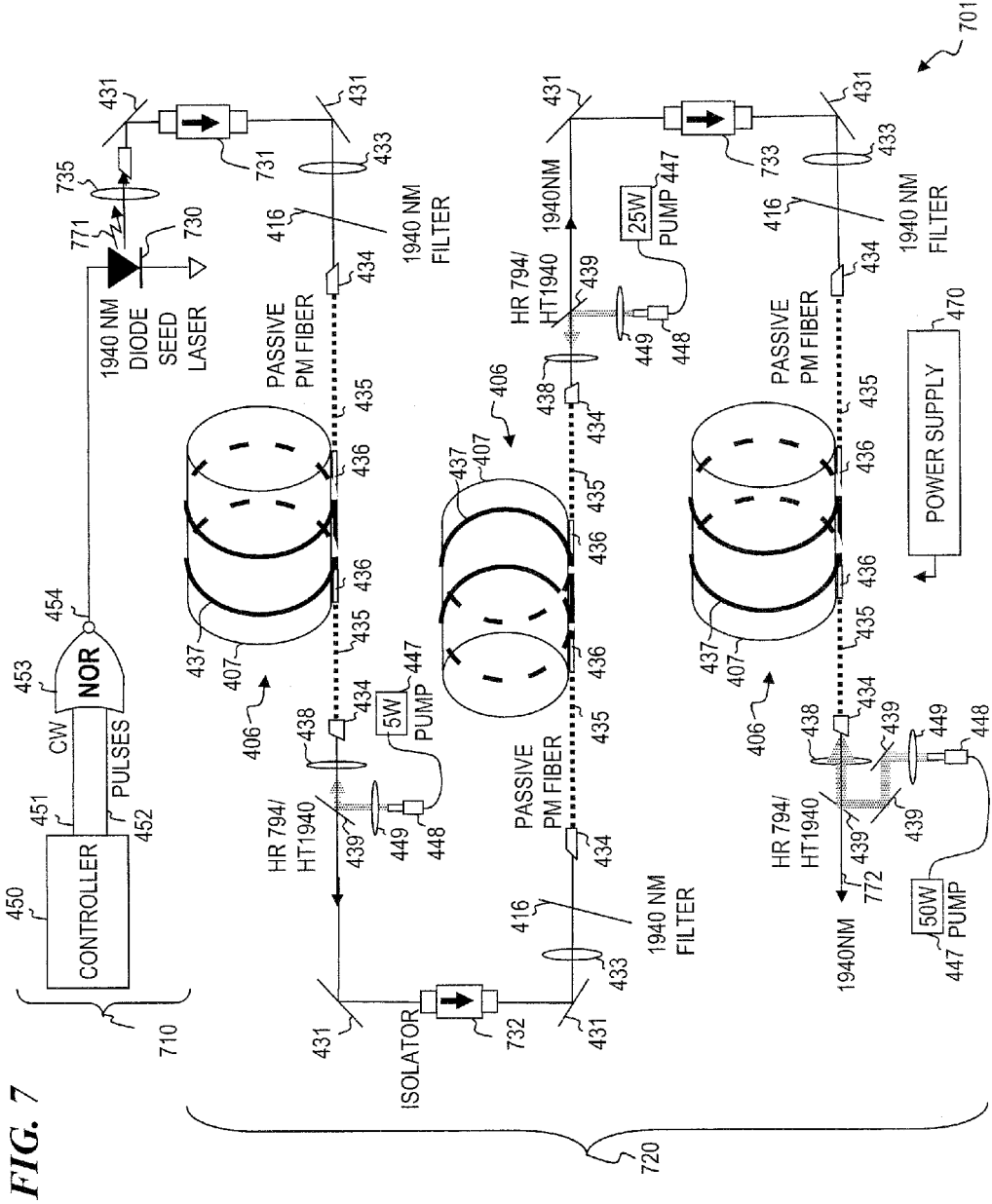
FIG. 7 is a schematic block diagram of a multiple-mode laser system 701 according to some embodiments of the invention.

FIG. 7 is a schematic block diagram of a multiple-mode laser system 701 according to some embodiments of the invention. In some embodiments, rather than a Q-switched master oscillator as described for FIG. 4, FIG. 5, FIG. 6 and FIG. 8, an electrically controlled laser diode 730 is used to generate CW or pulse seed signals, giving a much wider range of possible pulse lengths. Thus, in some embodiments, intermediate output signal 771 is reflected by zero or more reflectors 431 and passed through optional isolator 731 (used to prevent spurious backward traveling signal from the power amplifier from disrupting operation of the master oscillator 610. The signal light is then focused by lens 433 into endcap 434 of power amplifier fiber 406. In some embodiments, power amplifier fiber 406 includes a pair of passive PM fibers 435, one spliced to each end of active gain fiber 437 by splices 436. In some embodiments, gain fiber 437 is wound on a cooling mandrel 407. In some embodiments, a plurality of such power amplifier (PA) stages are provided (e.g., three such stages are shown in FIG. 7), in order to amplify seed signal 771 sufficiently to obtain the desired output power on signal 772.

In some embodiments, the signal output from the final power amplifier 406 is coupled out of the left endcap 434 and collimated by lens 438 to form an output beam 672 after passing through one of the dichroic mirrors 439. In some embodiments, one or more power amplifier pump lasers 447 (in some embodiments, these include a 5-watt semiconductor laser bar for the first PA stage, a 25-watt semiconductor laser bar for the second PA stage, and a 50-watt semiconductor laser bar for the final stage, that each generate pump light having a wavelength of approximately 794 nm, which is effectively absorbed by gain fiber 437 in order to amplify signal light 771 to form output signal beam 772.

In some embodiments, at each stage, pump light from pump 447 is delivered through endcap 448 and collimated by lens 449 and then reflected by one or more dichroic mirrors 439 and then through focusing lens 438 into endcap 434 in a counter-propagating direction relative to the signal light 577 in gain fiber 437.

In some embodiments, a portable power supply 470 (e.g., in some embodiments, power supply 470 includes a rechargeable battery) is used to supply electrical power to pump lasers 447 under the control of controller 450.

Figure 8:
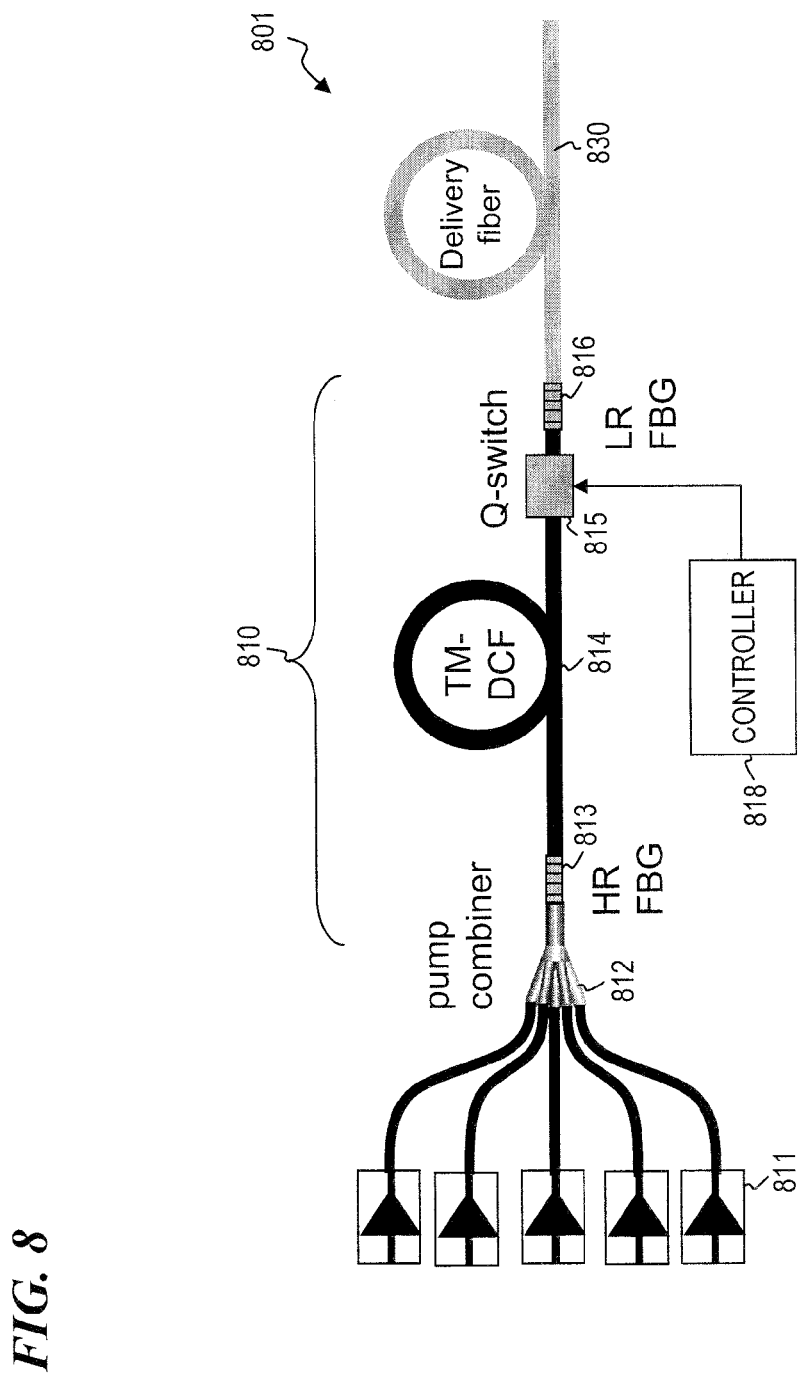
FIG. 8 is a schematic block diagram of a multiple-mode laser system 801 according to some embodiments of the invention.

FIG. 8 is a schematic block diagram of a multiple-mode laser system 801 according to some embodiments of the invention. In some embodiments, MMLS 801 includes a straight-line fiber laser 810 (a power oscillator, rather than a master oscillator followed by a power amplifier) that is driven by a plurality of pump lasers 811 whose outputs are combined by pump combiner 812 and launched through left-end fiber Bragg reflector 813 (which is high reflectivity (HR) at the signal wavelength). When Q-switch 815 is activated (to a pass mode) by controller 818, the signal light is amplified during many passes through Tm-doped double-clad optical fiber 814, such as any of the Tm-doped fibers described herein, and output through right-end fiber Bragg reflector 816 (which is low reflectivity (LR) at the signal wavelength). In some embodiments, a passive delivery fiber 830 is used to deliver the laser output signal to a handpiece such as described in FIGS. 3A-3F.

In some embodiments, the present invention provides a method and apparatus for aesthetic treatment of human tissue using a pulsed fiber laser.

In some embodiments, the present invention provides a method and apparatus wherein a pulsed fiber laser outputting short pulses applied to animal tissue induces the wound healing response from localized laser ablation and/or by inducing mechanical trauma with minimal thermal tissue damage and minimal thermal protein denaturation. In some embodiments, this results in less collateral damage to tissue than conventional longer-pulse-duration lasers that rely on thermal denaturation.

In some embodiments, the device of the present invention is used for treatment that includes applying laser pulses to highly vascular regions of sub-epidermal tissue (such as strawberry hemangioma, spider veins, telangiectasia, Karposi's sarcoma, and the like), as well as regions of dermis collagen mechanically damaged due to various reasons (such as frequent muscular contraction, burning, traumatic irritation, worsening of mechanical damage due to environmental exposure, and the like).

Some embodiments further include outputting the laser beam as a series of pulses wherein the laser beam has a pulse-repetition rate (PRR) of between about 0.01 kHz and about 500 kHz. In various embodiments, the PRR is about 10-20 Hz, about 20-50 Hz, about 50-100 Hz, about 100-200 Hz, about 200-500 Hz, about 500-1000 Hz, about 1-2 kHz, about 2-5 kHz, about 5-10 kHz, about 10-20 kHz, about 20-50 kHz, about 50-100 kHz, about 100-200 kHz, about 200-500 kHz, about 500-1000 kHz, or greater than 1 MHz.

Some embodiments further include outputting the laser beam pulses such that each pulse has a non-zero pulse energy of up to 100 µJ. In some embodiments, the present invention provides per-pulse energies of about 0.1-0.2 µJ about 0.2-0.5 µJ about 0.5-1 µJ, about 1-2 µJ, about 2-5 µJ about 5-10 µJ about 10-20 µJ about 20-50 µJ about 50-100 µJ, about 100-200 µJ, about 200-500 µJ or about 500-1000 µJ.

Some embodiments further include outputting the laser beam pulses such that each pulse has a non-zero pulse duration of about 100 ns or less. In various other embodiments, the present invention outputs pulse lengths of about 0.1-0.2 ns, about 0.2-0.5 ns, about 0.5-1 ns, about 1-2 ns, about 2-3 ns, about 3-4 ns, about 4-6 ns, about 6-8 ns, about 8-10 ns, about 10-20 ns, about 20-30 ns, about 30-40 ns, about 40-60 ns, about 60-80 ns, about 80-100 ns, about 100-200 ns, about 200-300 ns, about 300-400 ns, about 400-600 ns, about 600-800 ns, or about 800-1000 ns.

In some embodiments, the present invention provides a pulsed fiber laser that outputs laser pulses onto human tissue for treatment of one or more of the following: highly vascular regions of sub-epidermal tissue (such as strawberry hemangioma, spider veins, telangiectasia, Karposi's sarcoma, and the like), and/or regions of dermis collagen mechanically damaged due to various reasons (such as frequent muscular contraction, burning, traumatic irritation, worsening of mechanical damage due to environmental exposure, and the like).

In some embodiments, the present invention provides a pulsed fiber laser that outputs laser pulses onto human tissue having a wavelength range of between about 1.3 µm and about 2.5 µm and/or between about 3.5 µm and about 5.5 µm in order to output optical energy having a penetration depth in tissue of between about 0.2 mm and about 3 mm.

In some embodiments, the present invention provides a pulsed fiber laser that outputs laser pulses onto human tissue sufficient to achieve stress-confined tissue-penetration depth of between about 0.2 mm and about 3 mm. In some embodiments, the stress-confined tissue-penetration depth is about 2 mm. In some embodiments, the stress-confined tissue-penetration depth is between about 0.2 mm and about 0.4 mm. In some embodiments, the stress-confined tissue-penetration depth is between about 0.4 mm and about 0.6 mm. In some embodiments, the stress-confined tissue-penetration depth is between about 0.6 mm and about 0.8 mm. In some embodiments, the stress-confined tissue-penetration depth is between about 0.8 mm and about 1 mm. In some embodiments, the stress-confined tissue-penetration depth is between about 1 mm and about 1.2 mm. In some embodiments, the stress-confined tissue-penetration depth is between about 1.2 mm and about 1.4 mm. In some embodiments, the stress-confined tissue-penetration depth is between about 1.4 mm and about 1.8 mm. In some embodiments, the stress-confined tissue-penetration depth is between about 1.8 mm and about 2.2 mm. In some embodiments, the stress-confined tissue-penetration depth is between about 2.2 mm and about 2.6 mm. In some embodiments, the stress-confined tissue-penetration depth is between about 2.6 mm and about 3.0 mm. In some embodiments, the stress-confined tissue-penetration depth is at least about 3 mm.

In some embodiments, the pump wavelength is 795 nm, 808 nm, or 970 nm, depending on the media (in some embodiments, a silica-glass fiber or YA10 crystal) and/or user choice.

In some embodiments, the light from the thulium laser (e.g., short pulses having a wavelength of about 1.94 nm) are put through a fiber that also or alternatively carries pulses of visible and/or nerve-stimulating laser light such as described in U.S. patent application Ser. No. 11/536,639 filed Sep. 28, 2006 and titled "MINIATURE APPARATUS AND METHOD FOR OPTICAL STIMULATION OF NERVES AND OTHER ANIMAL TISSUE," U.S. Provisional Patent Application Ser. No. 60/872,930 filed Dec. 4, 2006 and titled "APPARATUS AND METHOD FOR CHARACTERIZING OPTICAL SOURCES USED WITH HUMAN AND ANI- MAL TISSUES," U.S. patent application Ser. No. 11/536,642 filed Sep. 28, 2006 and titled "APPARATUS AND METHOD FOR STIMULATION OF NERVES AND AUTOMATED CONTROL OF SURGICAL INSTRUMENTS," U.S. Provisional Patent Application Ser. No. 60/884,619 filed Jan. 11, 2007 and titled "VESTIBULAR IMPLANT USING INFRARED NERVE STIMULATION," each of which is incorporated herein by reference.

OTHER REFERENCES

Fried, N. M., Thulium fiber laser lithotripsy: An In vitro Analysis of stone fragmentation using a modulated 110-Watt thulium fiber laser at 1.94 µm. *Lasers in Surgery and Medicine.* 37(1):53-58, (2005)
Fried, N. M. and Murray, K. E., High-power thulium fiber laser ablation of urinary tissues at 1.94 µm. *Journal of Endourology* 19(1):25-31, 2005.
Itzkan, I., Albagli, D., Dark, M. L., Perelman, L. T., von Rosenberg, C., and Feld, M., The thermoelastic basis of short pulsed laser ablation of biological tissue, *Proc. National Academy of Sciences* USA 92: 1960-1964 (1995).
Jacques, S. L., Laser-tissue interactions. Photochemical, photothermal, and photomechanical. *Surg. Clin. North Am.,* 1992. 72(3): p. 531-58.
Thomsen, S., Pathologic analysis of photothermal and photomechanical effects of laser-tissue interactions. *Photochem. Photobiol.,* 1991. 53(6): p. 825-35.
Vogel, A., Venugopalan, V. Mechanisms of pulsed laser ablation of biological tissues. *Chem Rev.,* 2003. 103(5):577-644.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
a dual-mode laser device configured to operate in a first mode and a second mode, wherein, in the first mode, the dual-mode laser device generates CW or quasi-CW laser light that is configured to coagulate fluids in human tissue, wherein, in the second mode, the dual-mode laser device generates pulsed laser light, and wherein the pulsed laser light is configured to cause precise laser ablation of human tissues in an irradiated tissue zone within a medical procedure by localized stress-confined tissue damage that creates micropores in the tissue with minimal collateral damage outside the irradiated tissue zone, the dual-mode laser device including:
a rare-earth doped large-mode-area (LMA) first fiber gain-medium section, wherein the first fiber gain-medium section is configured to be optically pumped to generate a ring signal laser beam;
one or more passive polarization-maintaining (PM) fiber sections configured in series to form a ring optical signal path that extends through the first fiber gain-medium section, wherein the ring signal laser beam is propagated across the ring optical signal path; and
a Q-switch located between free-space parts in the ring optical signal path but outside of the first fiber gain-medium section, wherein the Q-switch is configured to generate the pulsed laser light of the second mode.

2. The apparatus of claim 1, wherein the device is wavelength tunable in the spectral range from 1.90-2.0 µm.

3. The apparatus of claim 1, wherein the rare-earth doped large-mode-area (LMA) first fiber gain-medium section is doped with thulium.

4. The apparatus of claim 1, wherein the ablation of the second mode includes removal of human tissue.

5. The apparatus of claim 1, wherein, in the second mode, the pulsed laserlight has a pulse-repetition rate of about 20 kHz.

6. The apparatus of claim 1, wherein, in the second mode, the pulsed laserlight has a pulse-repetition rate that is adjustable between about 0.001 Hz and about 100 kHz.

7. The apparatus of claim 1, wherein, in the second mode, each pulse of the pulsed laserlight has a pulse energy of about 5 mJ.

8. The apparatus of claim 1, wherein, in the second mode, each pulse of the pulsed laser light has a pulse energy that is adjustable to non-zero values up to about 50 mJ.

9. The apparatus of claim 1, wherein, in the second mode, each pulse of the pulsed laser light has a pulse duration tunable between 10-1000 nsec.

10. The apparatus of claim 1, further comprising an optical delivery fiber of about 100-µm diameter.

11. The apparatus of claim 1, further comprising an optical delivery fiber that is interchangeable with other delivery fibers having diameters from 50-1000 µm.

12. The apparatus of claim 1, wherein, in the second mode, the pulsed laser light creates a contiguous series of micropores along a line to be cut.

13. The apparatus of claim 1, wherein the dual-mode laser device is a fiber optic MOPA laser, and wherein the MOPA laser includes a ring laser master oscillator that outputs a signal wavelength of approximately 1.94 microns.

14. The apparatus of claim 1, wherein the dual-mode laser device is a fiber optic MOPA laser, and wherein the first fiber gain-medium section includes a polarization-maintaining Thulium-doped double-clad fiber having a core diameter of approximately 25 microns or larger.

15. The apparatus of claim 1, further comprising a semiconductor pump laser diode system that outputs pump light having a wavelength of approximately 794 nm, wherein the outputted pump light optically pumps the first fiber gain-medium section.

16. The apparatus of claim 1, further comprising a semiconductor pump laser diode system that outputs pump light, wherein the outputted pump light optically pumps the first fiber gain-medium section, wherein the dual-mode laser device further includes an isolator configured to control the ring signal laser beam such that it propagates in only a single direction around the ring optical signal path, and wherein the outputted pump light is launched into the first fiber gain-medium section in a direction that counter-propagates to the ring signal laser beam.

17. A dual-mode laser system comprising:
a dual-mode laser device configured to operate in a thermal-confinement mode and a stress-confinement mode, wherein, in the thermal-confinement mode, the dual-mode laser device is configured to coagulate fluids in human tissue, wherein, in the stress-confinement mode, the dual-mode laser device generates pulsed laser light, and wherein the pulsed laser light is configured to cause precise laser ablation of human tissues in an irradiated tissue zone within a medical procedure by localized stress-confined tissue damage that creates micropores in the tissue with minimal collateral damage outside the irradiated tissue zone, the dual-mode laser device including:
- a rare-earth doped large-mode-area (LMA) first fiber gain-medium section, wherein the first fiber gain-medium section is configured to be optically pumped to generate a ring signal laser beam;
- one or more passive polarization-maintaining (PM) fiber sections configured in series to form a ring optical signal path that extends through the first fiber gain-medium section, wherein the ring signal laser beam is propagated across the ring optical signal path;
- a Q-switch located between free-space parts in the ring optical signal path but outside of the first fiber gain-medium section, wherein the Q-switch is configured to generate the pulsed laser light of the stress-confinement mode;
- extraction optics configured to extract an intermediate optical signal beam from the ring signal laser beam in the ring optical signal path outside of the first fiber gain-medium section; and
- a second fiber gain-medium section operatively coupled to receive the intermediate optical signal beam and configured to be optically pumped in order to amplify the intermediate optical signal beam.

18. The laser system of claim 17, wherein the laser system is in a self-contained user-carriable unit, the unit having a battery that supplies power to the laser system for the coagulation of the thermal-confinement mode and for the ablation of the stress-confinement mode, and wherein, in the stress-confinement mode, the pulsed laser light creates a contiguous series of micropores along a line to be cut.

19. The laser system of claim 17, wherein, in the stress-confinement mode, the pulsed laser light has a pulse-repetition rate of about 20 kHz and creates a contiguous series of micropores along a line to be cut.

20. An apparatus comprising:
- a dual-mode laser device configured to operate in a first mode and a second mode, wherein, in the first mode, the dual-mode laser device generates CW or quasi-CW laser light that is configured to coagulate fluids in human tissue, wherein, in the second mode, the dual-mode laser device generates Q-switched-pulsed laser light, and wherein the Q-switched-pulsed laser light is configured to cause precise laser ablation of human tissue in an irradiated tissue zone by localized stress-confined tissue damage that creates micropores in the human tissue with minimal collateral damage outside the irradiated tissue zone, the dual-mode laser device including:
    - fiber-gain means for generating a ring signal laser beam;
    - means for forming a polarization-maintaining ring optical signal path that extends through the fiber-gain means for generating the ring signal laser beam, wherein the ring signal laser beam is propagated around the ring optical signal path; and
    - means for Q-switching the pulsed laser light in the second mode.

* * * * *